(12) United States Patent
Burkholz et al.

(10) Patent No.: US 10,525,237 B2
(45) Date of Patent: Jan. 7, 2020

(54) ERGONOMIC IV SYSTEMS AND METHODS

(71) Applicant: Becton, Dickinson and Company, Franklin Lakes, NJ (US)

(72) Inventors: Jonathan Karl Burkholz, Salt Lake City, UT (US); Bart D. Peterson, Farmington, UT (US); Stephen T. Bornhoft, Sandy, UT (US); Neville Chia, Singapore (SG); Siddharth Singh, Singapore (SG); Ralph L. Sonderegger, Farmington, UT (US); Bin Wang, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 325 days.

(21) Appl. No.: 15/286,292

(22) Filed: Oct. 5, 2016

(65) Prior Publication Data

US 2017/0120016 A1 May 4, 2017

Related U.S. Application Data

(60) Provisional application No. 62/247,626, filed on Oct. 28, 2015, provisional application No. 62/296,385, (Continued)

(51) Int. Cl.
*A61M 25/06* (2006.01)
*A61M 25/00* (2006.01)

(52) U.S. Cl.
CPC .... *A61M 25/0637* (2013.01); *A61M 25/0097* (2013.01); *A61M 25/0606* (2013.01); *A61M 25/0693* (2013.01); *A61M 2210/12* (2013.01)

(58) Field of Classification Search
CPC .......... A61M 25/0637; A61M 25/0606; A61M 25/0693
(Continued)

(56) References Cited

U.S. PATENT DOCUMENTS 3,046,984 A  7/1962 Eby
3,547,119 A  12/1970 Hall et al.
(Continued)

FOREIGN PATENT DOCUMENTS

CA  2 133 053 A1  3/1995
CN  101879341 A  11/2010
(Continued)

OTHER PUBLICATIONS

Silva, Elson, Email Regarding "Respecting Hydrology Science and IP Rights—US Pat. Application 20110130728," pp. 1-6 (Jun. 2, 2011).

*Primary Examiner* — Phillip A Gray
(74) *Attorney, Agent, or Firm* — Kirton & McConkie; Craig Metcalf; Kevin Stinger

(57) ABSTRACT

An IV catheter system may have a catheter component with a catheter hub, a cannula extending distally from the catheter hub, and a push feature adjacent to the catheter hub. The IV catheter system may also have a needle component with a needle hub, a needle extending distally from the needle hub along an axis, and a grip extending from the needle hub, generally parallel to the axis, with a pull feature. In the insertion configuration, the needle may be positioned within the cannula and the distal end of the needle hub may be seated in a needle port of the catheter hub. In the fluid delivery configuration, the needle may be positioned outside the catheter hub. The push and pull features may be positioned to facilitate manipulation with a single hand to move the IV catheter system from an insertion configuration to a fluid delivery configuration.

18 Claims, 7 Drawing Sheets

Related U.S. Application Data filed on Feb. 17, 2016, provisional application No. 62/247,596, filed on Oct. 28, 2015, provisional application No. 62/296,383, filed on Feb. 17, 2016, provisional application No. 62/247,599, filed on Oct. 28, 2015, provisional application No. 62/247,617, filed on Oct. 28, 2015, provisional application No. 62/247,607, filed on Oct. 28, 2015, provisional application No. 62/247,621, filed on Oct. 28, 2015, provisional application No. 62/247,624, filed on Oct. 28, 2015.

(58) Field of Classification Search
USPC .................................................. 604/168.01
See application file for complete search history.

(56) References Cited

U.S. PATENT DOCUMENTS

| | | | |
|---|---|---|---|
| 3,589,361 | A | 6/1971 | Loper et al. |
| 3,827,434 | A | 8/1974 | Thompson et al. |
| 3,853,127 | A | 12/1974 | Spademan |
| 3,859,998 | A | 1/1975 | Thomas et al. |
| 4,003,403 | A | 1/1977 | Nehring |
| 4,043,346 | A | 8/1977 | Mobley et al. |
| 4,099,528 | A | 7/1978 | Sorenson et al. |
| 4,149,539 | A | 4/1979 | Cianci |
| 4,172,448 | A | 10/1979 | Brush |
| 4,177,809 | A | 12/1979 | Moorehead |
| 4,193,399 | A | 3/1980 | Robinson |
| 4,200,096 | A | 4/1980 | Charvin |
| 4,269,186 | A | 5/1981 | Loveless et al. |
| 4,311,137 | A * | 1/1982 | Gerard .............. A61M 25/0606 604/122 |
| 4,317,445 | A | 3/1982 | Robinson |
| 4,326,519 | A * | 4/1982 | D'Alo .............. A61M 25/0637 604/165.04 |
| 4,353,369 | A | 10/1982 | Muetterties et al. |
| 4,362,156 | A | 12/1982 | Feller, Jr. et al. |
| 4,365,630 | A | 12/1982 | McFarlane |
| 4,387,879 | A | 6/1983 | Tauschinski |
| 4,419,094 | A | 12/1983 | Patel |
| 4,445,893 | A | 5/1984 | Bodicky |
| 4,449,693 | A | 5/1984 | Gereg |
| 4,496,348 | A | 1/1985 | Genese et al. |
| 4,525,157 | A | 6/1985 | Vaillancourt |
| 4,531,935 | A | 7/1985 | Berryessa |
| 4,682,980 | A | 7/1987 | Suzuki |
| 4,701,162 | A | 10/1987 | Rosenberg |
| 4,703,761 | A | 11/1987 | Rathbone et al. |
| 4,758,225 | A | 7/1988 | Cox et al. |
| 4,765,588 | A | 8/1988 | Atkinson |
| 4,772,264 | A | 9/1988 | Cragg |
| 4,813,939 | A | 3/1989 | Marcus |
| 4,834,708 | A | 5/1989 | Pillari |
| 4,842,591 | A | 6/1989 | Luther |
| 4,874,377 | A | 10/1989 | Newgard et al. |
| 4,894,052 | A | 1/1990 | Crawford |
| 4,917,668 | A | 4/1990 | Haindl |
| 4,917,671 | A | 4/1990 | Chang |
| 4,925,444 | A | 5/1990 | Orkin et al. |
| 4,935,010 | A | 6/1990 | Cox et al. |
| 4,950,257 | A | 8/1990 | Hibbs et al. |
| 4,966,586 | A | 10/1990 | Vaillancourt |
| D315,822 | S | 3/1991 | Ryan |
| 5,032,116 | A | 7/1991 | Peterson et al. |
| 5,041,097 | A | 8/1991 | Johnson |
| 5,053,014 | A | 10/1991 | Van Heugten |
| 5,057,087 | A | 10/1991 | Harmon |
| 5,059,186 | A | 10/1991 | Yamamoto et al. |
| 5,062,836 | A | 11/1991 | Wendell |
| 5,064,416 | A | 11/1991 | Newgard et al. |
| 5,084,023 | A | 1/1992 | Lemieux |
| 5,085,645 | A | 2/1992 | Purdy et al. |
| 5,108,374 | A | 4/1992 | Lemieux |
| 5,127,905 | A | 7/1992 | Lemieux |
| 5,135,504 | A | 8/1992 | McLees |
| 5,154,703 | A | 10/1992 | Bonaldo |
| 5,156,596 | A | 10/1992 | Balbierz et al. |
| 5,176,653 | A | 1/1993 | Metals |
| 5,176,662 | A | 1/1993 | Bartholomew et al. |
| 5,201,717 | A | 4/1993 | Wyatt et al. |
| 5,211,634 | A | 5/1993 | Vaillancourt |
| 5,215,525 | A | 6/1993 | Sturman |
| 5,215,528 | A | 6/1993 | Purdy et al. |
| 5,215,529 | A | 6/1993 | Fields et al. |
| 5,226,883 | A | 7/1993 | Katsaros et al. |
| 5,234,410 | A | 8/1993 | Graham et al. |
| 5,242,411 | A | 9/1993 | Yamamoto et al. |
| 5,254,097 | A | 10/1993 | Schock et al. |
| 5,267,971 | A | 12/1993 | Brimhall |
| 5,269,764 | A | 12/1993 | Vetter et al. |
| 5,273,546 | A | 12/1993 | McLaughlin et al. |
| 5,290,222 | A | 3/1994 | Feng et al. |
| 5,290,246 | A | 3/1994 | Yamamoto et al. |
| 5,295,969 | A | 3/1994 | Fischell et al. |
| 5,306,243 | A | 4/1994 | Bonaldo |
| 5,312,359 | A | 5/1994 | Wallace |
| 5,328,482 | A | 7/1994 | Sircom et al. |
| 5,330,435 | A | 7/1994 | Vaillancourt |
| 5,342,315 | A | 8/1994 | Rowe et al. |
| 5,350,363 | A | 9/1994 | Goode et al. |
| 5,352,205 | A | 10/1994 | Dales et al. |
| 5,356,381 | A | 10/1994 | Ensminger et al. |
| 5,368,029 | A | 11/1994 | Holcombe et al. |
| 5,405,323 | A | 4/1995 | Rogers et al. |
| 5,447,501 | A | 9/1995 | Karlsson et al. |
| 5,456,675 | A | 10/1995 | Wolbring et al. |
| 5,458,658 | A | 10/1995 | Sircom |
| 5,487,728 | A | 1/1996 | Vaillancourt |
| 5,498,241 | A * | 3/1996 | Fabozzi .............. A61M 25/0631 604/165.03 |
| 5,509,912 | A | 4/1996 | Vaillancourt et al. |
| 5,520,666 | A | 5/1996 | Choudhury et al. |
| 5,542,932 | A | 8/1996 | Daugherty |
| 5,549,566 | A | 8/1996 | Elias et al. |
| 5,549,576 | A | 8/1996 | Patterson et al. |
| 5,549,577 | A | 8/1996 | Siegel et al. |
| 5,562,631 | A | 10/1996 | Bogert |
| 5,562,633 | A | 10/1996 | Wozencroft |
| 5,573,510 | A | 11/1996 | Isaacson |
| 5,575,769 | A | 11/1996 | Vaillancourt |
| 5,575,777 | A | 11/1996 | Cover et al. |
| 5,584,809 | A | 12/1996 | Gaba |
| 5,599,310 | A | 2/1997 | Bogert |
| 5,601,536 | A | 2/1997 | Crawford et al. |
| 5,613,663 | A | 3/1997 | Schmidt et al. |
| 5,651,772 | A | 7/1997 | Arnett |
| 5,657,963 | A | 8/1997 | Hinchliffe et al. |
| 5,676,656 | A | 10/1997 | Brimhall |
| 5,690,612 | A | 11/1997 | Lopez et al. |
| 5,690,619 | A | 11/1997 | Erskine |
| 5,697,907 | A | 12/1997 | Gaba |
| 5,697,914 | A | 12/1997 | Brimhall |
| 5,697,915 | A | 12/1997 | Lynn |
| 5,699,821 | A | 12/1997 | Paradis |
| 5,700,244 | A | 12/1997 | Kriesel |
| 5,700,250 | A | 12/1997 | Erskine |
| 5,704,919 | A | 1/1998 | Kraus et al. |
| 5,718,688 | A | 2/1998 | Wozencroft |
| 5,730,123 | A | 3/1998 | Lorenzen et al. |
| 5,738,144 | A | 4/1998 | Rogers |
| 5,749,856 | A | 5/1998 | Zadini et al. |
| 5,749,861 | A | 5/1998 | Guala et al. |
| 5,772,636 | A | 6/1998 | Brimhall et al. |
| 5,800,399 | A | 9/1998 | Bogert et al. |
| 5,806,831 | A | 9/1998 | Paradis |
| 5,810,780 | A | 9/1998 | Brimhall et al. |
| 5,817,069 | A | 10/1998 | Arnett |
| 5,843,046 | A | 12/1998 | Motisi et al. |
| 5,853,393 | A | 12/1998 | Bogert |
| 5,882,345 | A | 3/1999 | Yoon |
| 5,911,710 | A | 6/1999 | Barry et al. |
| 5,935,109 | A | 8/1999 | Donnan |

(56) References Cited

U.S. PATENT DOCUMENTS

| | | |
|---|---|---|
| 5,935,110 A | 8/1999 | Brimhall |
| 5,947,932 A | 9/1999 | Desecki et al. |
| 5,954,698 A | 9/1999 | Pike |
| 5,961,497 A | 10/1999 | Larkin |
| 5,967,490 A | 10/1999 | Pike |
| 6,039,302 A | 3/2000 | Cote, Sr. et al. |
| 6,056,726 A | 5/2000 | Isaacson |
| 6,077,244 A | 6/2000 | Botich et al. |
| 6,117,108 A | 9/2000 | Woehr et al. |
| 6,142,981 A | 11/2000 | Heck et al. |
| 6,156,010 A | 12/2000 | Kuracina et al. |
| 6,171,287 B1 | 1/2001 | Lynn et al. |
| 6,206,851 B1 | 3/2001 | Prosl |
| 6,221,047 B1 | 4/2001 | Greene et al. |
| 6,224,569 B1 | 5/2001 | Brimhall |
| 6,273,869 B1 | 8/2001 | Vaillancourt |
| 6,287,278 B1 | 9/2001 | Woehr et al. |
| D451,599 S * | 12/2001 | Crawford ............... D24/112 |
| D451,600 S | 12/2001 | Crawford et al. |
| 6,379,332 B1 | 4/2002 | Van Landuyt |
| D458,678 S | 6/2002 | Cindrich |
| D458,994 S | 6/2002 | Cindrich |
| 6,440,119 B1 | 8/2002 | Nakada et al. |
| 6,461,362 B1 | 10/2002 | Halseth et al. |
| 6,485,473 B1 | 11/2002 | Lynn |
| 6,497,994 B1 | 12/2002 | Kafrawy |
| 6,506,181 B2 | 1/2003 | Meng et al. |
| D469,870 S | 2/2003 | Niermann et al. |
| 6,565,542 B2 | 5/2003 | Kumar et al. |
| 6,575,960 B2 | 6/2003 | Becker et al. |
| 6,595,954 B1 | 7/2003 | Luther et al. |
| 6,595,981 B2 | 7/2003 | Huet |
| 6,616,630 B1 | 9/2003 | Woehr et al. |
| 6,652,486 B2 | 11/2003 | Bialecki et al. |
| 6,663,592 B2 | 12/2003 | Rhad et al. |
| 6,689,102 B2 | 2/2004 | Greene |
| 6,695,814 B2 | 2/2004 | Greene et al. |
| 6,699,221 B2 | 3/2004 | Vaillancourt |
| 6,709,419 B2 | 3/2004 | Woehr |
| 6,719,726 B2 | 4/2004 | Meng et al. |
| 6,740,063 B2 | 5/2004 | Lynn |
| D491,266 S | 6/2004 | Cindrich et al. |
| D492,031 S | 6/2004 | Cindrich et al. |
| 6,749,588 B1 | 6/2004 | Howell et al. |
| D492,774 S | 7/2004 | Cindrich et al. |
| 6,837,884 B2 | 1/2005 | Woloszko |
| 6,883,778 B1 | 4/2005 | Newton et al. |
| 7,008,404 B2 | 3/2006 | Nakajima |
| 7,347,839 B2 | 3/2008 | Hiejima |
| 7,396,346 B2 | 7/2008 | Nakajima |
| 7,470,254 B2 | 12/2008 | Basta et al. |
| D592,302 S | 5/2009 | Stokes et al. |
| 7,670,317 B2 | 3/2010 | Cindrich et al. |
| 7,694,403 B2 * | 4/2010 | Moulton ........... A61M 25/0606 29/458 |
| 7,736,339 B2 | 6/2010 | Woehr et al. |
| 7,905,856 B2 | 3/2011 | McGuckin, Jr. et al. |
| 7,914,494 B2 | 3/2011 | Hiejima |
| 8,066,670 B2 | 11/2011 | Cluff et al. |
| 8,066,675 B2 | 11/2011 | Cindrich et al. |
| 8,070,725 B2 | 12/2011 | Christensen |
| 8,357,119 B2 | 1/2013 | Stout et al. |
| 8,361,020 B2 | 1/2013 | Stout et al. |
| 8,388,583 B2 | 3/2013 | Stout et al. |
| 8,574,203 B2 | 11/2013 | Stout et al. |
| 8,597,252 B2 | 12/2013 | Burkholz et al. |
| 8,641,675 B2 | 2/2014 | Stout et al. |
| 8,679,063 B2 | 3/2014 | Stout et al. |
| D713,522 S | 9/2014 | Woehr et al. |
| D819,802 S | 6/2018 | Burkholz et al. |
| D835,262 S | 12/2018 | Burkholz et al. |
| D837,368 S | 1/2019 | Burkholz et al. |
| 2001/0053895 A1 | 12/2001 | Vaillancourt |
| 2002/0072712 A1 | 6/2002 | Nool et al. |
| 2002/0082546 A1 | 6/2002 | Crank et al. |
| 2002/0177814 A1 | 11/2002 | Meng et al. |
| 2003/0083620 A1 | 5/2003 | Luther et al. |
| 2004/0078003 A1 | 4/2004 | Smith et al. |
| 2004/0092889 A1 | 5/2004 | Ferguson et al. |
| 2004/0102735 A1 | 5/2004 | Moulton et al. |
| 2004/0181192 A1 | 9/2004 | Cuppy |
| 2004/0193112 A1 | 9/2004 | Glazier et al. |
| 2004/0204681 A1 | 10/2004 | Thoresen et al. |
| 2004/0225260 A1 | 11/2004 | Villa et al. |
| 2004/0243060 A1 | 12/2004 | Rossi et al. |
| 2004/0243061 A1 | 12/2004 | McGurk |
| 2005/0273019 A1 | 12/2005 | Conway et al. |
| 2005/0277879 A1 | 12/2005 | Daga |
| 2006/0163515 A1 | 7/2006 | Ruschke |
| 2007/0043334 A1 | 2/2007 | Guala |
| 2007/0083157 A1 | 4/2007 | Belley et al. |
| 2007/0083162 A1 | 4/2007 | D'Reagan et al. |
| 2007/0093778 A1 | 4/2007 | Cindrich et al. |
| 2007/0191777 A1 | 8/2007 | King |
| 2007/0225648 A1 | 9/2007 | Winsor et al. |
| 2007/0233007 A1 | 10/2007 | Adams |
| 2008/0039796 A1 | 2/2008 | Nakajima |
| 2008/0108944 A1 | 5/2008 | Woehr |
| 2008/0132832 A1 | 6/2008 | McKinnon et al. |
| 2008/0167577 A1 | 7/2008 | Weilbacher et al. |
| 2008/0255473 A1 | 10/2008 | Dalebout et al. |
| 2008/0287906 A1 | 11/2008 | Burkholz et al. |
| 2009/0054845 A1 | 2/2009 | Puhasmagi et al. |
| 2009/0099431 A1 | 4/2009 | Dalebout et al. |
| 2009/0287189 A1 | 11/2009 | Suwito |
| 2010/0204648 A1 | 8/2010 | Stout et al. |
| 2010/0204675 A1 | 8/2010 | Woehr et al. |
| 2010/0222746 A1 | 9/2010 | Burkholz |
| 2010/0280455 A1 | 11/2010 | Ogawa et al. |
| 2011/0046570 A1 | 2/2011 | Stout et al. |
| 2011/0054403 A1 | 3/2011 | Tanabe et al. |
| 2011/0130728 A1 | 6/2011 | McKinnon |
| 2012/0016265 A1 | 1/2012 | Peterson et al. |
| 2012/0016307 A1 | 1/2012 | Burkholz et al. |
| 2012/0053523 A1 | 3/2012 | Harding |
| 2013/0090608 A1 | 4/2013 | Stout et al. |
| 2013/0218082 A1 | 8/2013 | Hyer et al. |
| 2013/0237925 A1 | 9/2013 | Trainer et al. |
| 2014/0046258 A1 | 2/2014 | Stout et al. |
| 2014/0107584 A1 | 4/2014 | Rosenberg et al. |
| 2014/0364809 A1 | 12/2014 | Isaacson et al. |
| 2015/0224296 A1 | 8/2015 | Winsor |
| 2017/0120008 A1 | 5/2017 | Burkholz et al. |
| 2017/0120014 A1 | 5/2017 | Harding et al. |
| 2017/0216535 A1 | 8/2017 | Mao |
| 2017/0347913 A1 | 12/2017 | Isaacson et al. |

FOREIGN PATENT DOCUMENTS

| | | |
|---|---|---|
| CN | 102440822 A | 5/2012 |
| CN | 102716541 A | 10/2012 |
| CN | 203852671 | 10/2014 |
| DE | 20 2009 009 602 U1 | 12/2009 |
| EP | 0 268 480 A1 | 5/1988 |
| EP | 0 732 120 A1 | 9/1996 |
| EP | 0 812 601 A2 | 12/1997 |
| EP | 0 993 839 A1 | 4/2000 |
| EP | 1 306 097 | 5/2003 |
| EP | 1 679 043 A1 | 7/2006 |
| EP | 1 884 257 A1 | 2/2008 |
| EP | 1 944 049 A1 | 7/2008 |
| EP | 2022421 | 2/2009 |
| EP | 2 044 970 A1 | 4/2009 |
| EP | 2 327 434 A1 | 6/2011 |
| GB | 2508466 A | 6/2014 |
| JP | S56102253 | 8/1981 |
| JP | S5832774 | 2/1983 |
| JP | H06-086821 | 3/1994 |
| JP | H09-509075 | 9/1997 |
| JP | 2000279527 | 10/2000 |
| JP | 2004528127 | 9/2004 |
| JP | 2011045544 | 3/2011 |
| JP | 2012521796 | 9/2012 |
| JP | 2012200425 | 10/2012 |

(56) References Cited

FOREIGN PATENT DOCUMENTS

| | | |
|---|---|---|
| JP | 3188771 | 1/2014 |
| JP | 2014108112 | 6/2014 |
| WO | 88/07388 A1 | 10/1988 |
| WO | 97/45151 | 12/1997 |
| WO | 98/42393 A1 | 10/1998 |
| WO | 99/34849 A1 | 7/1999 |
| WO | 01/12254 A1 | 2/2001 |
| WO | 02/096495 | 12/2002 |
| WO | 2004/032995 A2 | 4/2004 |
| WO | 2004/082727 | 9/2004 |
| WO | 2004/087247 | 10/2004 |
| WO | 2004/098685 A1 | 11/2004 |
| WO | 2006/037638 A1 | 4/2006 |
| WO | 2007/052655 | 5/2007 |
| WO | 2008/022258 A2 | 2/2008 |
| WO | 2008/045761 A2 | 4/2008 |
| WO | 2008/052790 A2 | 5/2008 |
| WO | 2008/058132 A2 | 5/2008 |
| WO | 2008/058133 A2 | 5/2008 |
| WO | 2009/114833 A1 | 9/2009 |
| WO | 2010/093791 A1 | 8/2010 |
| WO | 2010/111283 | 9/2010 |
| WO | 2010/111285 A1 | 9/2010 |
| WO | 2011/055287 | 5/2011 |
| WO | 2011/109542 A1 | 9/2011 |
| WO | 2016/007442 | 1/2016 |
| WO | 2017/062579 | 4/2017 |

* cited by examiner

ERGONOMIC IV SYSTEMS AND METHODS

RELATED APPLICATIONS

This application claims the benefit of U.S. Provisional Application No. 62/247,626, which was filed on Oct. 28, 2015, U.S. Provisional Application No. 62/296,385, which was filed on Feb. 17, 2016, U.S. Provisional Patent Application No. 62/247,596, which was filed on Oct. 28, 2015, U.S. Provisional Patent Application No. 62/296,383, which was filed on Feb. 17, 2016, U.S. Provisional Patent Application No. 62/247,599, which was filed Oct. 28, 2015, U.S. Provisional Patent Application No. 62/247,617, which was filed on Oct. 28, 2015, U.S. Provisional Patent Application Ser. No. 62/247,607, which was filed Oct. 28, 2015, U.S. Provisional Patent Application Ser. No. 62/247,621, which was filed Oct. 28, 2015, and U.S. Provisional Patent Application Ser. No. 62/247,624, which was filed Oct. 28, 2015, each of which is incorporated herein by reference in their entirety.

BACKGROUND

The present invention is generally directed to systems and methods for intravenous ("IV") delivery, by which fluids can be administered directly to the vascular system of a patient. More particularly, the present invention is directed to IV catheter systems and methods that facilitate insertion into the patient and/or motion from an insertion configuration to a fluid delivery configuration in which fluid can be delivered to the patient through the IV catheter system. An IV catheter system according to the invention is used broadly herein to describe components used to deliver the fluid to the patient, for use in arterial, intravenous, intravascular, peritoneal, and/or non-vascular administration of fluid. Of course, one of skill in the art may use an IV catheter system to administer fluids to other locations within a patient's body.

Known IV catheter systems and methods have a number of deficiencies. Many such systems require the clinician to use two hands to position the IV catheter system and/or insert the needle into the fluid delivery location on the patient (for example, the vein into which fluid is to be delivered). Further, many such systems require the clinician to use two hands to move the IV catheter system from the insertion configuration to a fluid delivery configuration, in-which the needle is removed from the cannula to permit fluid to be delivered to the vein through the cannula. Thus, the clinician is required to stabilize the patient's arm or other body part having the fluid delivery location prior to insertion of the IV catheter system. As a result, extra time is required for the clinician to initiate transfusion. Further, the clinician is unable to perform any other task, such as stabilizing or reassuring the patient, during insertion and/or motion to the fluid delivery configuration.

Accordingly, there is a need for IV catheter systems and methods that facilitate IV catheter system placement, insertion, and/or preparation for fluid delivery. There is a further need for such IV catheter systems that are inexpensive, easy to manufacture, and versatile.

BRIEF SUMMARY OF THE INVENTION

Embodiments of the present invention are generally directed to an IV catheter system with enhanced ergonomics. In some embodiments, the IV catheter system may be inserted and moved to a fluid delivery configuration with only one hand. The IV catheter system may include a catheter component and a needle component. The catheter component may have a catheter hub having a catheter hub distal end and a catheter hub proximal end. The catheter hub may define a chamber extending between the catheter hub distal end and the catheter hub proximal end and a needle port at the catheter hub proximal end that provides access to the chamber. The catheter hub may also have a cannula extending distally from the catheter hub distal end and a push feature connected to the catheter hub and defining a push surface of the catheter component. The needle component may have a needle hub having a needle hub distal end and a needle extending distally from the needle hub distal end. The needle component may also have a pull feature connected to the needle hub and defining a pull surface of the needle component. In the insertion configuration, the needle may be positioned within the cannula, the needle hub distal end may be seated in the needle port, and the pull surface may be positioned distal the catheter hub proximal end.

The pull surface may be positioned distal the push surface when the IV catheter system is in the insertion configuration.

The push feature may include a feature such as a trailing edge of a wing secured to the catheter hub with the wing being generally parallel to an axis of the cannula, a grip feature applied to or formed on a major surface of a wing secured to the catheter hub with the wing being generally parallel to an axis of the cannula; a series of nubs applied to or formed on a major surface of a wing secured to the catheter hub with the wing being generally parallel to an axis of the cannula, a tab secured to a wing secured to the catheter hub generally parallel to an axis of the cannula with the tab extending from the wing in a direction nonparallel to the wing, a tab secured to a wing secured to the catheter hub generally parallel to an axis of the cannula with the tab extending substantially perpendicularly from the wing, a tab secured to and extending outwardly from the catheter hub, a circumferential ring disposed around the catheter hub, or a proximal surface of an extension tubing junction extending from the catheter hub.

The push feature may be integrated into a securement platform such as a wing extending from the catheter hub generally parallel to a cannula axis along which the cannula extends such that, in the fluid delivery configuration, the wing rests on skin of a patient receiving fluid through the IV catheter system.

The wing may be integrated with an extension tubing junction extending outwardly from the catheter hub at a location intermediate the catheter hub distal end and the catheter hub proximal end.

The wing is optionally not coplanar with a cannula axis containing the cannula. Alternatively, the wing is coplanar with a cannula axis containing the cannula.

The catheter component may further include a septum within the chamber through which the needle passes in the insertion configuration. The septum may be configured to provide a sufficiently low resistance to withdrawal of the needle through the septum to enable a single hand of a clinician to move the IV catheter system from the insertion configuration to the fluid delivery configuration without assistance of another hand of the clinician.

The pull feature may include a feature such as a leading edge of a grip secured to the needle hub and extending outwardly and generally distally from the needle hub, a grip feature applied to or formed on a major surface of a grip secured to the needle hub and extending outwardly and generally distally from the needle hub, a series of nubs applied to or formed on a major surface of a grip secured to the needle hub and extending outwardly and generally distally from the needle hub, a tab secured to a grip secured to the needle hub and extending outwardly and generally distally from the needle hub generally parallel to an axis of the needle with the tab extending from the grip in a direction nonparallel to the grip, and a tab secured to a grip secured to the needle hub and extending outwardly and generally distally from the needle hub generally parallel to an axis of the needle with the tab extending substantially perpendicularly from the grip.

The catheter component may have a wing extending outwardly from the catheter hub generally parallel to a cannula axis. The needle component may have a grip extending outwardly and distally from the needle hub generally parallel to a needle axis. In the insertion configuration, the wing and the grip may be generally parallel to each other and may be positioned in abutting relation to each other. During motion of the IV catheter system from the insertion configuration to the fluid delivery configuration, the grip may slide along the wing.

The needle component may have a rotation stop feature formed proximate the needle hub distal end. The rotation stop feature may be configured to engage a corresponding feature on the catheter component to limit rotation of the needle component relative to the catheter component.

The catheter component may include a wing extending outwardly from the catheter hub generally parallel to a cannula axis. The needle component may include a grip extending outwardly and distally from the needle hub generally parallel to a needle axis. A rotation stop feature may extend distally from the needle hub distal end. In the insertion configuration, the needle component may be rotated relative to the catheter component such that the rotation stop feature contacts the wing of the catheter component and the grip is substantially co-planar with the wing. The rotation stop feature may allow the grip to be rotated overtop the wing but not underneath the wing.

A gripping or push surface may comprise a circumferential ring extending around one or more surfaces of the catheter hub. A low-drag septum may be disposed within the catheter hub. Opposed side grips may be disposed on opposing sides of the needle hub. A low-volume, high-visualization flash chamber may be removably attached to a flash receptacle attached to a proximal end of the needle hub.

The needle component may have a needle hub proximal end having a flash receptacle containing a flash chamber. The flash receptacle may include one or more end and/or side vents for venting air from the flash chamber.

In other embodiments, the IV catheter system may be inserted and moved to a fluid delivery configuration with only one hand. The IV catheter system may include a catheter component and a needle component. The catheter component may include a catheter hub with a catheter hub distal end and a catheter hub proximal end, the catheter hub defining a chamber extending between the catheter hub distal end and the catheter hub proximal end. The catheter component may also include a needle port at the catheter hub proximal end that provides access to the chamber and a cannula extending distally from the catheter hub distal end. The catheter component may also include a wing connected to the catheter hub and extending outwardly from the catheter hub, the wing having a push surface of the catheter component. The needle component may have a needle hub having a needle hub distal end and a needle extending distally from the needle hub distal end. The needle component may also have a grip connected to the needle hub and extending outwardly and distally from the needle hub, the grip comprising a pull surface of the needle component. In the insertion configuration, the needle may be positioned within the cannula, the needle hub distal end may be seated in the needle port, and the pull surface may be positioned distal the catheter hub proximal end.

The pull surface may be positioned distal the push surface when the IV catheter system is in the insertion configuration. The push surface may be a surface such as a trailing edge of the wing, a grip feature applied to or formed on a major surface of the wing, a series of nubs applied to or formed on a major surface of the wing, a tab secured to the wing and extending from the wing in a direction nonparallel to the wing, a tab secured to the wing and extending substantially perpendicularly from the wing, or a proximal surface of an extension tubing junction extending from the catheter hub and integrated with the wing.

The pull surface may be a surface such as a leading edge of the grip, a grip feature applied to or formed on a major surface of the grip, a series of nubs applied to or formed on a major surface of the grip, a tab secured to the grip and extending from the grip in a direction nonparallel to the grip, or a tab secured to the grip and tab extending substantially perpendicularly from the grip.

In other embodiments, the IV catheter system may include a rotation stop feature that limits rotation of the needle component relative to the catheter component. The IV catheter system may include a catheter component and a needle component. The catheter component may have a catheter hub having a proximal end, a cannula that extends distally from the catheter hub, and a wing that extends outwardly from a side of the catheter hub. The needle component may have a needle hub having a distal end that couples to the proximal end of the catheter hub, a needle that extends distally from the distal end of the needle hub, and a grip that extends outwardly and distally from a side of the needle hub. The needle component may also have a rotation stop feature formed at the distal end of the needle hub, the rotation stop feature being adapted to contact a corresponding feature of the catheter component, such as the wing of the catheter component or another external feature or tab on the catheter component's proximal end to limit rotation of the needle component with respect to the catheter component when the needle is fully inserted in the cannula.

The rotation stop feature may extend distally from the distal end of the needle hub. When the rotation stop feature contacts the wing, a plane of the grip may be substantially parallel to a plane of the wing.

In other embodiments, the IV catheter system may be inserted and moved to the fluid delivery configuration with only one hand. The IV catheter system may have a catheter component and a needle component. The catheter component may have a catheter hub with a catheter hub distal end and a catheter hub proximal end. The catheter hub may be shaped to define a chamber extending between the catheter hub distal end and the catheter hub proximal end, and a needle port at the catheter hub proximal end that provides access to the chamber. The catheter component may also have a cannula extending distally from the catheter hub distal end along a cannula axis, and a push feature positioned proximate the catheter hub to define a push surface oriented substantially perpendicular to the cannula axis. The needle component may have a needle hub with a needle hub distal end and a needle hub proximal end, a needle extending distally from the needle hub distal end along a needle axis, and a grip extending from the needle hub, generally parallel to the axis. The grip may have a pull feature. In an insertion configuration, the needle may be positioned within the cannula and the needle hub distal end may be seated in the needle port. In a fluid delivery configuration, the needle may be positioned outside the catheter hub. The push feature and the pull feature may be positioned to receive contact from digits of a single hand to urge the IV catheter system to move from the insertion configuration to the fluid delivery configuration.

The catheter hub may have a catheter hub intermediate portion between the catheter hub proximal end and the catheter hub distal end. The catheter component may further have an extension tubing junction extending outwardly from the catheter hub intermediate portion to connect the catheter hub to extension tubing.

The catheter component may further have a securement platform with a first wing extending from the catheter hub, generally parallel to the cannula axis. In the fluid delivery configuration, the first wing may rest on skin of a patient receiving fluid through the IV catheter system. The first wing may be integrated with the extension tubing junction.

The catheter component may further have a septum within the chamber, through which the needle passes in the insertion configuration. The septum may be configured to provide a sufficiently low resistance to withdrawal of the needle through the septum to enable the hand, alone, to move the IV catheter system from the insertion configuration to the fluid delivery configuration.

The catheter component may further have a securement platform with a first wing extending from the catheter hub, generally parallel to the cannula axis. In the fluid delivery configuration, the first wing may rest on skin of a patient receiving fluid through the IV catheter system.

The push feature may be a tab secured to the first wing. The tab may extend from the first wing along a direction nonparallel to the first wing.

In the insertion configuration, the first wing and the grip may be generally parallel to each other and may be positioned in abutting relation to each other. During motion of the IV catheter system from the insertion configuration to the fluid delivery configuration, the grip may slide along the first wing.

The push feature may be a tab secured to the catheter hub. The tab may extend outwardly from the catheter hub.

The tab may be positioned proximate the catheter hub proximal end. Specifically, the tab may be positioned closer to the catheter hub proximal end than to the catheter hub distal end.

The pull feature may be a leading edge of the grip. The leading edge may be shaped and sized to comfortably receive contact from one of the digits.

The pull feature may be a tab secured to the grip. The tab may extend from the grip along a direction nonparallel to the grip.

The IV catheter system may further have a flash receptacle secured to the needle hub proximal end. The flash receptacle may be shaped to define a flash chamber that receives blood in response to positioning of a distal end of the cannula in a blood vessel.

In other embodiments, the IV catheter system may be inserted and moved to the fluid delivery configuration with only one hand. The IV catheter system may have a catheter component and a needle component. The catheter component may have a catheter hub with a catheter hub distal end and a catheter hub proximal end. The catheter hub may be shaped to define a chamber extending between the catheter hub distal end and the catheter hub proximal end. The catheter hub may further have a needle port at the catheter hub proximal end that provides access to the chamber. The catheter component may further have a cannula extending distally from the catheter hub distal end along a cannula axis, a push feature positioned proximate the catheter hub, and a securement platform with a first wing extending from the catheter hub, generally parallel to the cannula axis. In a fluid delivery configuration, the first wing may rest on skin of a patient receiving fluid through the IV catheter system. The first wing may not be coplanar with the cannula axis. The needle component may have a needle hub with a needle hub distal end and a needle hub proximal end, a needle extending distally from the needle hub distal end along a needle axis, and a grip extending from the needle hub, generally parallel to the needle axis. The grip may have a pull feature. In an insertion configuration, the needle may be positioned within the cannula and the needle hub distal end may be seated in the needle port. In the fluid delivery configuration, the needle may be positioned outside the catheter hub. The push feature and the pull feature may be positioned to receive contact from digits of a single hand to urge the IV catheter system to move from the insertion configuration to the fluid delivery configuration.

The catheter hub may have a catheter hub intermediate portion between the catheter hub proximal end and the catheter hub distal end. The catheter component may further have an extension tubing junction extending outwardly from the catheter hub intermediate portion to connect the catheter hub to extension tubing.

The catheter component may further have a securement platform with a first wing extending from the catheter hub, generally parallel to the cannula axis. In the fluid delivery configuration, the first wing may rest on skin of a patient receiving fluid through the IV catheter system. The first wing may be integrated with the extension tubing junction.

The catheter component may further have a septum within the chamber, through which the needle passes in the insertion configuration. The septum may be configured to provide a sufficiently low resistance to withdrawal of the needle through the septum to enable the single hand, alone, to move the IV catheter system from the insertion configuration to the fluid delivery configuration.

The push feature may be a tab secured to the first wing. The tab may extend from the first wing along a direction nonparallel to the first wing.

In other embodiments, the IV catheter system may be inserted and moved to the fluid delivery configuration with only one hand. The IV catheter system may have a catheter component and a needle component. The catheter component may have a catheter hub with a catheter hub distal end and a catheter hub proximal end. The catheter hub may be shaped to define a chamber extending between the catheter hub distal end and the catheter hub proximal end, and a needle port at the catheter hub proximal end that provides access to the chamber. The catheter component may further have a cannula extending distally from the catheter hub distal end along a cannula axis, and a push feature positioned proximate the catheter hub. The needle component may have a needle hub with a needle hub distal end and a needle hub proximal end, a needle extending distally from the needle hub distal end along a needle axis, and a first grip extending from the needle hub, generally parallel to the needle axis. The first grip may have a first pull feature positioned distally of the needle hub distal end. The needle component may further have a second grip extending from the needle hub, generally parallel to the needle axis. The second grip may have a second pull feature positioned proximally of the first pull feature. In an insertion configuration, the needle may be positioned within the cannula and the needle hub distal end may be seated in the needle port. In a fluid delivery configuration, the needle may be positioned outside the catheter hub. The push feature, the first pull feature, and the second pull feature may be positioned to receive contact from digits of a single hand to urge the IV catheter system to move from the insertion configuration to the fluid delivery configuration.

The second grip may be substantially coplanar with the first grip. The second grip may further be positioned on an opposite side of the catheter hub from the first grip.

The catheter component may further have a securement platform with a first wing extending from the catheter hub, generally parallel to the cannula axis. In the fluid delivery configuration, the first wing may rest on skin of a patient receiving fluid through the IV catheter system. In the insertion configuration, the first wing and the first grip may be generally parallel to each other and may be positioned in abutting relation to each other. During motion of the IV catheter system from the insertion configuration to the fluid delivery configuration, the first grip may slide along the first wing.

In other embodiments, the IV catheter system may include a rotation stop feature that limits rotation of the needle component with respect to the catheter component. The IV catheter system may have a catheter component and a needle component. The catheter component may have a catheter hub and a cannula that extends distally from the catheter hub. The catheter component may further have an extension tubing junction which extends outwardly from a first side of the catheter hub and couples extension tubing to the catheter hub. The catheter component may also have and a first wing that extends outwardly from the first side. The needle component may have a needle hub having a distal end that couples to a proximal end of the catheter hub and a needle that extends distally from the needle hub. The needle component may also have a grip that extends outwardly from a second side of the needle hub and a rotation stop feature formed at the distal end of the needle hub. The rotation stop feature may contact the catheter component to limit rotation of the needle component with respect to the catheter component.

The rotation stop feature may include a feature on the needle hub and a corresponding feature on the catheter hub. The feature on the needle hub may extend distally from the distal end of the needle hub, may be an external feature at the distal end of the needle hub, or may be an internal feature at the distal end of the needle hub. The feature on the needle hub and/or the corresponding feature on the catheter hub may each comprise a single surface or feature, or alternatively may each comprise a plurality of compatible surfaces or features. The feature on the catheter hub may be an external feature or tab on the catheter hub, and may be a feature of the catheter hub that serves additional purposes, such as the first wing of the catheter system. The rotation stop feature may extend distally from the distal end of the needle hub and contact the first wing of the catheter component. When the rotation stop feature contacts the first wing, the grip may be substantially in-line with the first wing. The rotation stop feature may allow the grip to be rotated overtop the first wing but not underneath the first wing. The rotation stop feature may form a ledge that contacts an underside of the first wing.

The grip may include a pull feature and the first wing may include a push feature. A proximal end of the needle component may include a flash receptacle containing a flash chamber. The flash receptacle may include one or more side vents for venting air from the flash chamber. The flash receptacle may also include a proximal opening for venting air from the flash chamber. The flash receptacle may be removable from the needle hub.

In other embodiments, the IV catheter system may include a flash receptacle having one or more side vents for venting air from within the flash chamber. The IV catheter system may have a catheter component and a needle component. The catheter component may include a catheter hub and a cannula that extends distally from the catheter hub. The catheter component may also include an extension tubing junction which extends outwardly from a first side of the catheter hub and couples extension tubing to the catheter hub and a first wing that extends outwardly from the first side. The needle component may include a needle hub having a distal end that couples to a proximal end of the catheter hub, a needle that extends distally from the needle hub, and a grip that extends outwardly from a second side of the needle hub. The needle hub may further include a flash receptacle formed at a proximal end of the needle component and including a flash chamber. The flash receptacle may include one or more side vents for venting air from within the flash chamber. The flash receptacle may also include a proximal opening for venting air from within the flash chamber.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

Figure 1:
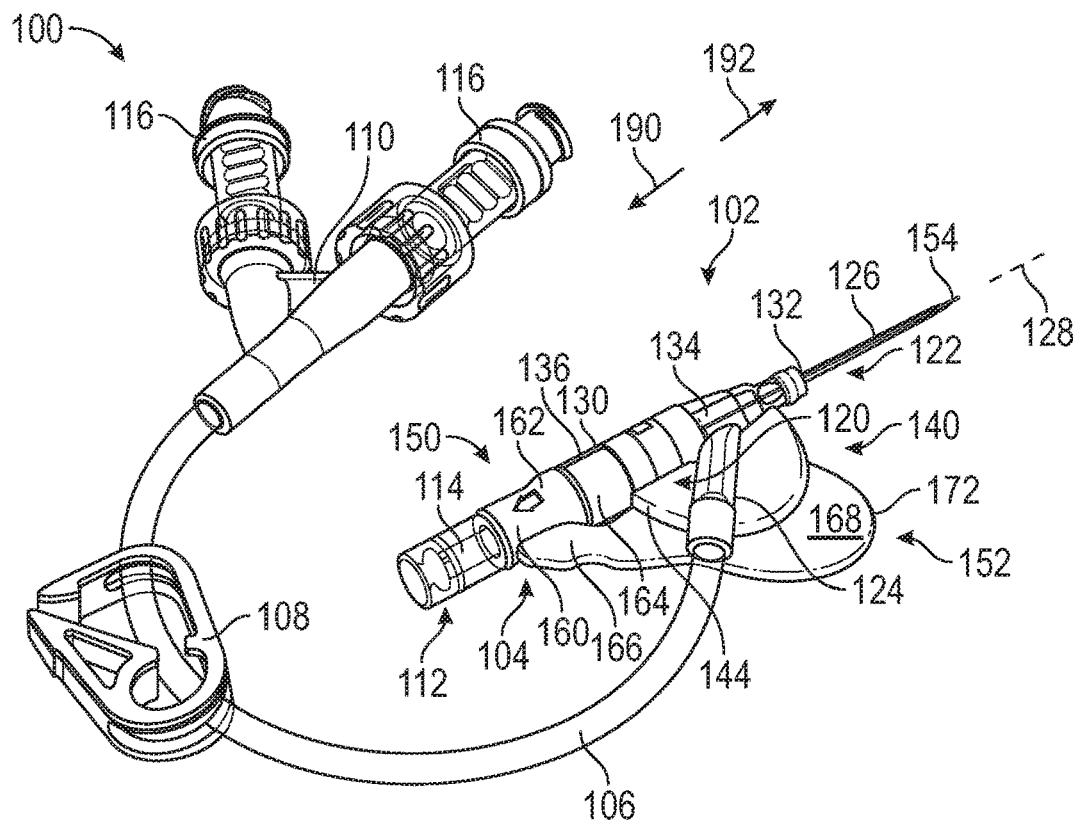
FIG. 1 is a perspective view of an IV catheter system according to one embodiment.

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal," "top," "up," or "upwardly" refers to a location on the device that is closest to the clinician using the device and farthest from the patient in connection with whom the device is used when the device is used in its normal operation. Conversely, the term "distal," "bottom," "down," or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device. Further, as used herein, a "cannula" is a tube that can be inserted into the body for delivery and/or removal of fluid. A cannula may be rigid or flexible, and may be formed of any material, including but not limited to metals, ceramics, polymers, elastomers, and composite materials.

As used herein, the term "connected," "attached," or "secured," and the like when used to refer to the relationship of one component with respect to another component are intended primarily to define a spatial relationship unless otherwise indicated, and should be understood to embrace instances where the two components are integrally formed with each other as well as instances when the two components are separately formed and then later secured to one another.

FIG. 1 is a perspective view of an IV catheter system 100 according to one embodiment. The IV catheter system 100 may be connected to a supply of fluid to be infused. The fluid supply (not shown) may include a bag of blood or medication to be delivered to the patient, a drip chamber that regulates flow of the fluid to the IV catheter system 100, and/or other components involved with the supply of fluid to the IV catheter system 100. The IV catheter system 100 may have a number of components, as shown in the exemplary embodiment of FIG. 1. These components may include a catheter component 102, a needle component 104, an extension tube 106, a clamp 108, a Y adapter 110, and/or a flash receptacle 112.

The catheter component 102 may be inserted into the fluid delivery location in the patient in order to convey the fluid to the patient. The needle component 104 may facilitate insertion of the catheter component 102 to the fluid delivery location. The extension tube 106 may convey the fluid to the catheter component 102. The clamp 108 may be used to manually block fluid flow to the catheter component 102 when it is desired to stop or pause fluid delivery. The Y adapter 110 may have luer lock fittings that are readily connected to the fluid supply and/or other fluid-carrying components, for example, via connection to a complementary luer lock (not shown) of the fluid supply or other fluid components. The flash receptacle 112 may have a flash chamber 114 that receives blood when the IV catheter system 100 has been positioned to access a blood vessel. The flash receptacle 112 may thus indicate proper insertion of the IV catheter system 100.

As embodied in FIG. 1, the IV catheter system 100 may be an integrated IV catheter system, as the extension tube 106 is pre-attached to the catheter component 102. In other embodiments, IV catheter systems of various open, integrated, and/or safety integrated configurations may be used.

The catheter component 102 may have various components, which may include a catheter hub 120, a securement platform 122, an extension tubing junction 124, and a cannula 126. The catheter hub 120 may have a generally tubular and/or hollow conical configuration, and may have a proximal end 130 and a distal end 132. The catheter hub 120 may be shaped to define a chamber 134 through which the fluid flows to reach the fluid delivery location. The catheter hub 120 may have a needle port 136 at the proximal end 130. The chamber 134 may contain a septum (not visible) that is designed to block flow of blood and/or the fluid to be delivered from the chamber 134 through the needle port 136. The cannula 126 may be secured to the distal end 132 of the catheter hub 120, and may extend distally of the distal end 132 along a cannula axis 128.

The securement platform 122 may have a generally planar configuration designed to permit the securement platform 122 to be secured to the skin of the patient, proximate the fluid delivery location, to keep the catheter component 102 securely in place as fluid delivery takes place. As embodied in FIG. 1, the securement platform 122 may have a first wing 140 with a generally planar shape, and the plane of the first wing 140 may be generally parallel the cannula axis 128. The first wing 140 may be fixedly secured to the catheter hub 120, and may have a generally semicircular shape when viewed from along a direction perpendicular to the plane of the first wing 140. The first wing 140 may have a trailing edge 144 oriented toward the proximal end 130 of the catheter hub 120, with the trailing edge 144 forming or capable of being used as a push surface. Other surfaces of the first wing 140 and/or the securement platform 122 may also optionally serve as a push surface. The first wing 140 and/or the push surface of the first wing 140 are examples of a push feature of the catheter component 102. As part of the securement platform 122, the first wing 140 may be adapted to rest on skin of a patient receiving fluid through the IV catheter system 100.

In alternative embodiments (not shown), a securement platform may also include a second wing, which may optionally be coplanar with the first wing 140. Such a second wing may extend in the opposite direction, relative to the catheter hub, from the first wing 140. If desired, the second wing may be symmetrical to the first wing 140. Such a second wing may also have a trailing edge that can be used as a push surface, in addition to or in the alternative to use of the trailing edge 144 of the first wing 140. The second wing may provide additional options for gripping the catheter component 102 for insertion and/or motion to the fluid delivery configuration, and is another example of a push feature.

The first wing 140 may not be coplanar with the cannula axis 128 but may, instead, be offset from the cannula axis 128. Thus, the first wing 140 may not intersect the midline of the catheter hub 120. Alternatively, the first wing 140 may be coplanar with the cannula axis 128. The first wing 140 may be integrated with the extension tubing junction 124 such that the extension tubing junction 124 divides the first wing 140 into a leading portion and a trailing portion having the trailing edge 144. Thus, the axis of the extension tubing junction 124 may also not be coplanar with the cannula axis 128, but may rather be coplanar with the first wing 140 and offset from the cannula axis 128. Alternatively, the axis of the extension tubing junction 124 may be coplanar with the cannula axis and the first wing 140, or with only one of them.

The needle component 104 may have a needle hub 150, a grip 152, and a needle 154. The needle hub 150 may be detachably coupled to the catheter hub 120 of the catheter component 102. The grip 152 may extend outward from the needle hub 150. The needle 154 may be removably positioned within the cannula 126 such that the needle 154 facilitates the process of accessing the fluid delivery location (for example, a vein) and proper positioning of the cannula 126 to deliver the fluid to the fluid delivery location. The needle 154 may extend distally from the needle hub 150 along a needle axis, which may be coincident with the cannula axis 128 when the IV catheter system 100 is in an insertion configuration, as shown in FIG. 1.

The needle hub 150 may have a generally tubular shape with a proximal end 160 and a distal end 162. The needle hub 150 may have a boss 164 positioned at the distal end 162; the boss 164 may be insertable into the needle port 136 of the catheter hub 120 of the catheter component 102.

The grip 152 may have a generally planar shape that extends outward from the needle hub 150. Additionally, the grip 152 may extend distally from the needle hub 150. When viewed from a direction perpendicular to the plane of the grip 152, the grip 152 may have an oblong and/or partially elliptical shape, with a proximal portion 166 with a relatively narrow shape, and a distal portion 168 with a broader shape. The proximal portion 166 may extend outward from the needle hub 150, coplanar with the needle axis (and thus coplanar with the cannula axis 128 when the IV catheter system 100 is in the insertion configuration). Alternatively, the grip 152 may extend generally outward and distally from the needle hub 150 without being coplanar with the needle axis, and a plane of the grip 152 may optionally be generally parallel to the needle axis. The grip 152 and the first wing 140 may have one or more grip features (not shown), which may help provide a secure interface that facilitates gripping and/or moving the grip 152 by hand relative to the first wing 140. The grip features are one example of features that may serve as a push feature or a pull feature. The grip 152 may have a leading edge 172, which may form or serve as a pull surface of the needle component 104, and the leading edge 172 is another example of a pull feature.

The IV catheter system 100 is illustrated in FIG. 1 in the insertion configuration, in which the IV catheter system 100 is readily insertable to position the cannula 126 in the fluid delivery location. The IV catheter system 100 also has a fluid delivery configuration, in which the fluid flow through the cannula 126 is relatively unimpeded. In the insertion configuration, the needle 154 is positioned within the cannula 126 to provide a sharpened tip for penetrating tissue and a relatively stiff body that supports the cannula 126 during insertion. The boss 164 of the needle hub 150 is positioned within the needle port 136 of the catheter hub 120. The needle 154 passes through the septum (not shown) of the catheter component 102. Additionally, the pull feature of the needle component 104 (e.g. leading edge 172) is positioned distally of the proximal end 130 of the catheter component 102 as well as distally of the push feature of the catheter component 102 (e.g. trailing edge 144).

The IV catheter system 100 may be inserted into position by positioning the tip of the cannula 126 proximate the fluid delivery location (for example, the patient's vein). The securement platform 122 may be placed on the patient's skin, proximate the fluid delivery location and/or held in the clinician's hand. The catheter component 102 and the needle component 104 may be advanced together to push the cannula 126 until the tip of the cannula 126 penetrates the surrounding tissue and reaches the fluid delivery location. If desired, the catheter component 102 may be advanced by pushing a push surface of the catheter component 102. The "push surface" is a surface that is generally proximally oriented, and thus can receive contact from the clinician's hand to urge the catheter component 102 and the needle component 104, together, distally.

Once the tip of the cannula 126 has reached the fluid delivery location, the IV catheter system 100 may be moved to the fluid delivery configuration. This may be done by withdrawing the needle component 104 proximally from the catheter component 102. This may initially cause the boss 164 to be withdrawn proximally from within the needle port 136. The needle 154 may also be withdrawn proximally from the cannula 126, and then through the chamber 134, including the septum (not shown). The needle 154 may pass out of the chamber 134 through the needle port 136, thus completing motion of the IV catheter system 100 to the fluid delivery configuration. Fluid flow to the fluid delivery location may now be accomplished by urging the fluid to flow through the extension tube 106, into the chamber 134, and through the cannula 126 to the fluid delivery location.

The IV catheter system 100 may advantageously be designed to facilitate insertion to the fluid delivery location with a single hand. For example, during insertion, the clinician may, with one hand, hold the catheter component 102 and the needle component 104, for example, by grasping the securement platform 122 and the grip 152. The clinician may then, with the same hand, apply gentle pressure to one or more push surfaces of the catheter component 102 (for example, the trailing edge 144 of the first wing 140) to urge the tip of the cannula 126 to penetrate the patient's skin and ultimately reach the fluid delivery location. If desired, one or more locking features (not shown) may be used to hold the catheter component 102 and the needle component 104 together until the clinician applies a threshold force to move the IV catheter system 100 from the insertion configuration to the fluid delivery configuration. Such locking features may take the form of interlocking features (not shown) between the boss 164 and the needle port 136, and/or the like.

The IV catheter system 100 may be designed to provide visual confirmation of proper placement in a blood vessel. For example, at least a portion of the catheter hub 120 may be translucent to provide visibility into the chamber 134. Thus, when the tip of the cannula 126 enters a vein, the resulting blood flow, or "flash," may be visible through the exterior wall of the catheter hub 120 as the blood enters the chamber 134. The extension tubing junction 124 and the extension tube 106 may also, optionally, be translucent. In some embodiments, the flash may extend through the extension tube 106 to the Y adapter 110. The Y adapter 110 may be coupled to the fluid supply in a manner that substantially prevents blood leakage. Further, the flash receptacle 112 may indicate flash by receiving blood within the flash chamber 114. If desired, the flash receptacle 112 may be vented so that it can be disconnected from the needle component 104 without discharging collected blood. This may help reduce infection risk and/or facilitate use of the flash receptacle 112 to collect blood samples for testing.

Further, the IV catheter system 100 may advantageously be designed to facilitate motion from the insertion configuration to the fluid delivery configuration with a single hand. For example, the clinician may, with a single hand, which may be the same hand used to insert the IV catheter system 100 into the fluid delivery location, grasp the catheter component 102 and the needle component 104 and withdraw the needle component 104 proximally from the catheter component 102. The catheter component 102 may be left substantially in place so that only the needle component 104 moves significantly to move the IV catheter system 100 from the insertion configuration to the fluid delivery configuration.

This may be done by placing digits of the hand to contact the pull surface(s) of the needle component 104 and the push surface(s) of the catheter component 102, and then with those digits, pulling the needle component 104 proximally (as indicated by the arrow 190) while pushing or bracing the catheter component 102 distally (as indicated by the arrow 192) relative to the needle component 104 to keep it from moving proximally with the needle component 104. For example, the trailing edge 144 of the first wing 140 or of the securement platform 122 may act as a push surface, while the leading edge 172 of the grip 152 may act as a pull surface. The clinician may place one or more fingers on the leading edge 172 of the grip 152 and pull proximally, while pushing and/or bracing with a thumb and/or one or more other fingers on the trailing edge 144 of the first wing 140 of the securement platform 122. Thus, the catheter component 102 may be kept in place with the tip of the cannula 126 at the fluid delivery location while the needle component 104 is withdrawn proximally from the catheter component 102 to unblock the fluid delivery path to the fluid delivery location.

The relative positions of the pull and push surfaces may facilitate single-handed operation in the manner described above. The offset of the first wing 140 from the cannula axis 128 (or alternatively of the grip 152 from the needle axis) may also facilitate such single-handed operation by ensuring that the first wing 140 and the grip 152 are spaced apart, thereby providing adequate space for a digit to contact the trailing edge 144 without interference from the grip 152, and to contact the leading edge 172 without interference from the first wing 140. The relative distal/proximal positions of the one or more push surfaces of the catheter component 102 and the one or more pull surfaces of the needle component 104 may facilitate one-handed movement to the fluid delivery position. If desired, the coupling of the needle hub 150 with the catheter hub 120 may be such that the needle hub 150 is rotatable relative to the catheter hub 120 while the IV catheter system 100 is in the insertion configuration. Thus, the clinician may, with the hand, rotate the grip 152 to an orientation that is most comfortable for pulling on the leading edge 172, prior to pulling on the leading edge 172 and pushing and/or bracing on the trailing edge 144.

The septum (not shown) may have a "low friction" or "low drag" design configured to provide relatively low resistance to withdrawal of the needle 154 proximally through the septum, which occurs as the IV catheter system 100 transitions from the insertion configuration to the fluid delivery configuration. The resistance to withdrawal of the needle 154 through the septum may be sufficiently low that the clinician can relatively easily move the IV catheter system 100 from the insertion configuration to the fluid delivery configuration with only a single hand. In some embodiments, the resistance to withdrawal may be, on average, less than about 50 gf.

Figure 2A:
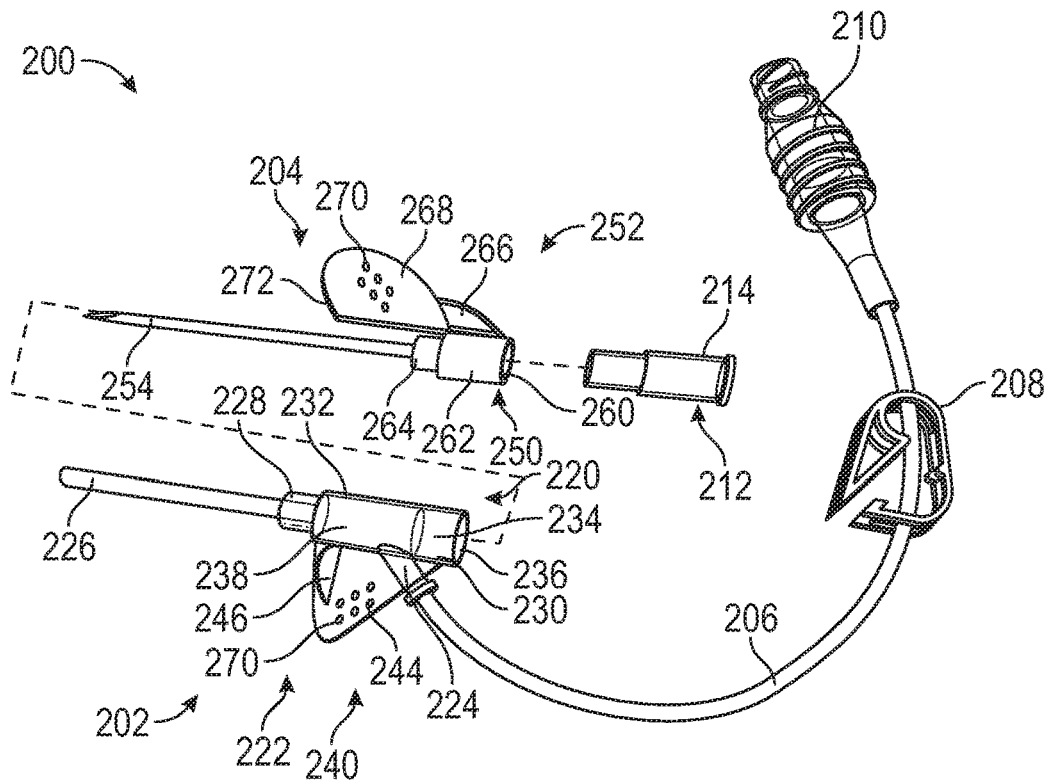
FIGS. 2A and 2B are an exploded perspective view of an IV catheter system according to one alternative embodiment, and a fully assembled view of a portion of the IV catheter system, respectively.
Figure 2B:
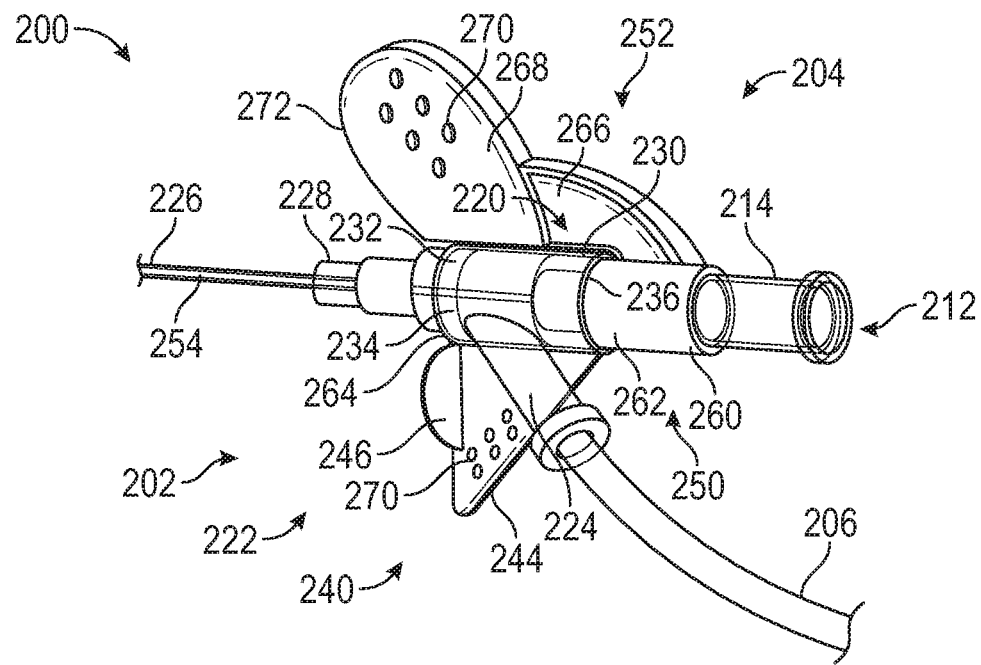

FIGS. 2A and 2B are an exploded perspective view of an IV catheter system 200 according to one alternative embodiment, and a fully assembled view of a portion of the IV catheter system 200, respectively. The IV catheter system 200 may have components that generally correspond to those of the IV catheter system 100 of FIG. 1. As shown in FIG. 2A, the IV catheter system 200 may have a catheter component 202, a needle component 204, an extension tube 206, a clamp 208, a luer lock adapter 210, and a flash receptacle 212. The luer lock adapter 210 may be similar to the Y adapter 110, but may include only a single fitting designed to be connected to a fluid source or other component. FIG. 2B illustrates only the catheter component 202, the needle component 204, and the distal end of the extension tube 206 connected to the catheter component 202. The IV catheter system 200 may have a configuration similar to that of the IV catheter system 100 of FIG. 1; however, some components may be modified, added, or omitted to provide alternative ergonomics and/or functionality.

The catheter component 202 may have a catheter hub 220, a securement platform 222, an extension tubing junction 224, and a cannula 226. The catheter hub 220 may have a generally tubular and/or hollow conical shape, with a proximal end 230 and a distal end 232. The catheter hub 220 may have a generally translucent exterior wall shaped to define a chamber 234 through which fluid flows to reach the fluid delivery location through the cannula 226. The catheter hub 220 may have a needle port 236 that connects to the needle component 204, proximate the proximal end 230 of the catheter hub 220. The catheter hub 220 may also have a septum 238 positioned within the chamber 234. The septum 238 may be a "low drag" septum as described previously.

Further, the catheter hub 220 may have a kink resistance feature that helps to avoid kinking of the cannula 226 during insertion and/or infusion. The kink resistance feature may take the form of a proximal extension 228 on the distal end 232 of the catheter hub 220. The proximal extension 228 may receive the cannula 226, and may provide some resistance to bending of the cannula 226 at the juncture of the cannula 226 to the distal end 232 to relieve the bending strain of the cannula 226 at that location, thereby helping avoid kinking or other undesired bending of the cannula 226. If desired, the proximal extension 228 may be formed of a more flexible material than that of the remainder of the catheter hub 220, so as to allow some flexure to help prevent kinking.

The securement platform 222 may be attached to the skin of the patient during fluid delivery to keep the cannula 226 in place at the fluid delivery location. The securement platform 222 may have a first wing 240, which may be generally planar in shape. The first wing 240 may have a generally triangular shape when viewed from perpendicular to the plane of the first wing 240, with a trailing edge 244 that can act as a push surface. As in the previous embodiment, the first wing 240 may optionally be offset from a cannula axis (not shown) of the cannula 226. Alternatively, if desired, the first wing 240 may be coplanar with the cannula axis. Similarly, the first wing 240 may be integrated with or merely adjacent to the extension tubing junction 224.

A tab 246 may be secured to the first wing 240. The tab 246 may be integrally formed with the first wing 240, or may be formed separately from the first wing 240 and attached to the first wing 240 through any of various methods known in the art. The tab 246 may extend substantially perpendicular to the plane of the first wing 240, or at a modest angle away from perpendicular to the plane of the first wing 240 (e.g. any angle small enough from perpendicular to allow a proximally oriented surface of the tab 246 to continue to serve as a push surface). Thus, the proximally oriented surface of the tab 246 may serve as a push surface, and may be oriented substantially perpendicular to the cannula axis (not shown) of the cannula 226 or at a modest angle away from perpendicular to the cannula axis as described. Alternatively, the tab 246 may extend from the first wing 240 along a direction nonparallel to the plane of the first wing 240.

The needle component 204 may have a needle hub 250, a grip 252, and a needle 254. The needle hub 250 may have a generally cylindrical shape with a proximal end 260 and a distal end 262. The needle hub 250 may also have a boss 264 that protrudes from the distal end 262 to interface with the needle port 236 of the catheter hub 220.

The grip 252 may have a generally planar shape, with an irregular, elongated shape when viewed from perpendicular to the plane of the grip 252. The grip 252 may have a proximal portion 266 with a relatively narrow shape, and a distal portion 268 with an enlarged shape. The proximal portion 266 may extend outward from the needle hub 250, and may be generally coplanar with the needle axis (not shown), and thus with the axis of the needle hub 250. The distal portion 268 of the grip 252 may have a leading edge 272, which may serve as a pull surface. The grip 252 and/or the first wing 240 may have one or more grip features 270, such as raised nubs, bumps, or ridges of any desirable shape and number, or a high-friction surface applied to the first wing 240 or from which a portion of the first wing 240 may be formed, which may help provide a secure interface that facilitates gripping and/or moving the grip 252 and/or the first wing 240 by hand. The grip features 270 are an example of a feature that may serve as a push feature or a pull feature.

The grip 252 and the first wing 240 may be rotatable, relative to each other, about the cannula axis of the cannula 226 and the needle axis of the needle 254, which may be coincident in the insertion configuration shown in FIG. 2B. Thus, the clinician may rotate the grip 252 and/or the first wing 240 to the desired relative orientation prior to insertion and/or prior to motion to the fluid delivery configuration. In one method, the clinician may rotate the grip 252 such that the extension tubing junction 224 and/or the tab 246 are sandwiched between the grip 252 and the first wing 240.

The flash receptacle 212 may function in a manner similar to that of the flash receptacle 112 of the previous embodiment. Specifically, when the distal end of the cannula 226 enters a blood vessel, blood may flow through the catheter hub 220, through the needle hub 250, and into a flash chamber 214 of the flash receptacle 212. Thus, the clinician may have visual confirmation of proper placement of the distal end of the cannula 226.

To move the IV catheter system 200 from the insertion configuration to the fluid delivery configuration, the clinician may position a digit (for example, a finger) on the leading edge 272 of the grip 252, and a digit (for example, a finger or thumb) on the trailing edge 244 of the first wing 240 and/or the proximally oriented surface of the tab 246. The clinician may then pull the leading edge 272 of the grip 252 proximally, and may push and/or brace the trailing edge 244 of the first wing 240 and/or the proximally oriented surface of the tab 246 distally. This may cause the catheter component 202 to remain in place while the needle component 204 is withdrawn proximally from the catheter component 202.

Figure 3:
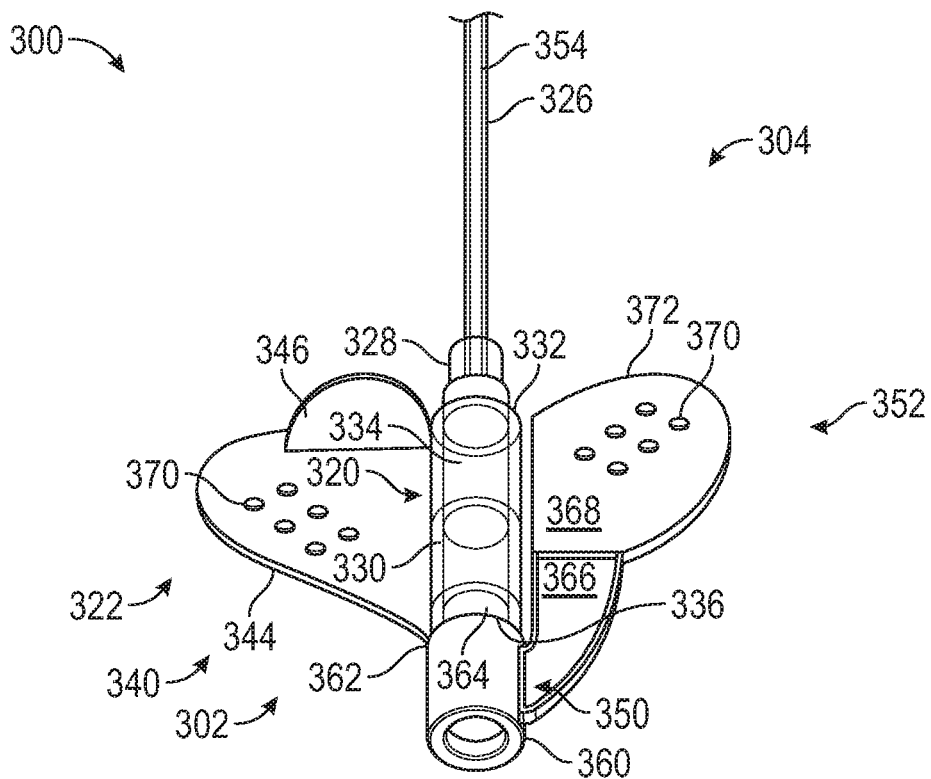
FIG. 3 is a perspective views of a portion of an IV catheter system according to another alternative embodiment.

FIG. 3 is a perspective view of a portion of an IV catheter system 300 according to another alternative embodiment. The IV catheter system 300 may have components that generally correspond to those of the IV catheter systems of previous embodiments. FIG. 3 shows only a catheter component 302 and a needle component 304. The IV catheter system 300 may be of an "open" type rather than an "integrated type," and may thus not have pre-attached extension tubing. Rather, extension tubing may be coupled to the proximal end of the catheter component 302 to supply the fluid. The IV catheter system 300 may otherwise have a configuration similar those of previous embodiments; however, some components may be modified, added, or omitted to provide alternative ergonomics and/or functionality.

The catheter component 302 may have a catheter hub 320, a securement platform 322, and a cannula 326. The catheter hub 320 may have a generally tubular and/or hollow conical shape, with a proximal end 330 and a distal end 332. The catheter hub 320 may have a generally translucent exterior wall shaped to define a chamber 334 through which fluid flows to reach the fluid delivery location through the cannula 326. The catheter hub 320 may have a needle port 336 that connects to the needle component 304, proximate the proximal end 330 of the catheter hub 320. The catheter hub 320 may also have a septum (not shown) positioned within the chamber 334. The septum may be a "low drag" septum as described previously. No extension tubing junction may be present, since the extension tubing is to be coupled to the proximal end 330 of the catheter hub 320.

Further, the catheter hub 320 may have a kink resistance feature that helps to avoid kinking of the cannula 326 during insertion and/or infusion. The kink resistance feature may take the form of a proximal extension 328 on the distal end 332 of the catheter hub 320. The proximal extension 328 may receive the cannula 326, and may provide some resistance to bending of the cannula 326 at the juncture of the cannula 326 to the distal end 332 to relieve the bending strain at that location, thereby helping avoid kinking or other undesired bending of the cannula 326. If desired, the proximal extension 328 may be formed of a more flexible material than that of the remainder of the catheter hub 320, so as to allow some flexure to help prevent kinking.

The securement platform 322 may be attached to the skin of the patient during fluid delivery to keep the cannula 326 in place at the fluid delivery location. The securement platform 322 may have a first wing 340, which may be generally planar in shape. The first wing 340 may have a generally triangular shape when viewed from perpendicular to the plane of the first wing 340, with a trailing edge 344 that can act as a push surface. The first wing 340 may be coplanar with the cannula axis (not shown) of the cannula 326.

A tab 346 may be secured to the first wing 340. The tab 346 may be integrally formed with the first wing 340, or may be formed separately from the first wing 340 and attached to the first wing 340 through any of various methods known in the art. The tab 346 may extend substantially perpendicular to the plane of the first wing 340 or at a modest angle away from perpendicular to the plane of the first wing 340 (e.g. any angle small enough to allow a proximally oriented surface of the tab 346 to serve as a push surface). Alternatively, the tab 346 may extend from the first wing 340 along a direct nonparallel to the first wing 340. Thus, the proximally oriented surface of the tab 346 may serve as a push surface, and may be oriented substantially perpendicular to the cannula axis (not shown) of the cannula 326 or at a modest angle away from perpendicular to the cannula axis as described.

The needle component 304 may have a needle hub 350, a grip 352, and a needle 354. The needle hub 350 may have a generally cylindrical shape with a proximal end 360 and a distal end 362. The needle hub 350 may also have a boss 364 that protrudes from the distal end 362 to interface with the needle port 336 of the catheter hub 320.

The grip 352 may have a generally planar shape, with an irregular, elongated shape when viewed from perpendicular to the plane of the grip 352. The grip 352 may have a proximal portion 366 with a relatively narrow shape, and a distal portion 368 with an enlarged shape. The proximal portion 366 may extend outward from the needle hub 350, and may be generally coplanar with the needle axis (not shown), and thus with the axis of the needle hub 350. The distal portion 368 of the grip 352 may have a leading edge 372, which may serve as a pull surface. The grip 352 and/or the first wing 340 may have one or more grip features 370, such as raised nubs, bumps, or ridges of any desirable shape and number, or a high-friction surface applied to the first wing 340 or from which a portion of the first wing 340 may be formed, which may help provide a secure interface that facilitates gripping and/or moving the grip 352 and/or the first wing 340 by hand.

The grip 352 and the first wing 340 may be rotatable, relative to each other, about the cannula axis of the cannula 326 and the needle axis of the needle 354, which may be coincident in the insertion configuration shown in FIG. 3. Thus, the clinician may rotate the grip 352 and/or the first wing 340 to the desired relative orientation prior to insertion and/or prior to motion to the fluid delivery configuration. In one method, the clinician may rotate the grip 352 relative to the first wing 340 such that the tab 346 is sandwiched between the grip 352 and the first wing 340.

If desired, the IV catheter system 300 may have a flash receptacle (not shown), which may be similar to those of previous embodiments. The flash receptacle may receive blood to provide visual confirmation of proper placement of the distal end of the cannula 326.

To move the IV catheter system 300 from the insertion configuration to the fluid delivery configuration, the clinician may position a digit (for example, a finger) on the leading edge 372 of the grip 352, and a digit (for example, a finger or thumb) on the trailing edge 344 of the first wing 340 and/or the proximally oriented surface of the tab 346. The clinician may then pull the leading edge 372 proximally, and may push and/or brace the trailing edge 344 of the first wing 340 and/or the proximally oriented surface of the tab 346 distally. This may cause the catheter component 302 to remain in place while the needle component 304 is withdrawn proximally from the catheter component 302.

Figure 4:
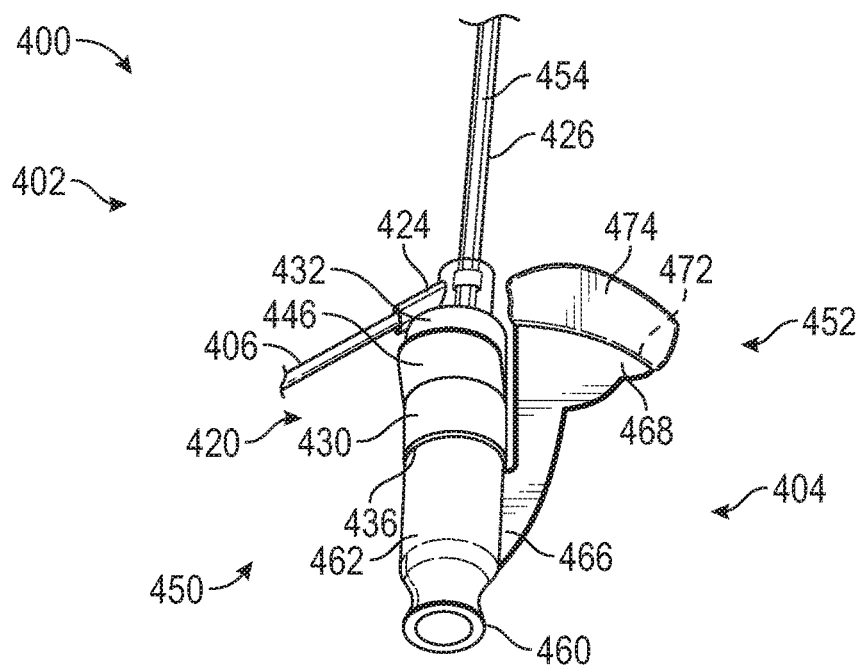
FIG. 4 is a perspective view of an IV catheter system according to another alternative embodiment.

FIG. 4 is a perspective view of an IV catheter system 400 according to another alternative embodiment. The IV catheter system 400 may have components that generally correspond to those of the IV catheter systems of previous embodiments. FIG. 4 shows only a catheter component 402, a needle component 404, and an extension tube 406. The IV catheter system 400 may have a configuration similar to those of the IV catheter systems of previous embodiments; however, some components may be modified, added, or omitted to provide alternative ergonomics and/or functionality.

The catheter component 402 may have a catheter hub 420, an extension tubing junction 424, and a cannula 426. The catheter hub 420 may have a generally tubular and/or hollow conical shape, with a proximal end 430 and a distal end 432. The catheter hub 420 may have an exterior wall shaped to define a chamber (not shown) through which fluid flows to reach the fluid delivery location through the cannula 426. The catheter hub 420 may have a needle port 436 that connects to the needle component 404, proximate the proximal end 430 of the catheter hub 420. The catheter hub 420 may also have a septum (not shown) positioned within the chamber. The septum may be a "low drag" septum as described previously.

The catheter component 402 may not have a securement platform. Rather, if desired, the catheter hub 420 may be attached directly to the skin of the patient. Alternatively, any system or method known in the art for catheter stabilization may be applied to the catheter component 402 during fluid delivery to keep the catheter component 402 in place. As another alternative, the extension tubing junction 424 may be used to facilitate comfortable placement of the catheter component 402 on the patient's skin and/or attachment of the catheter component 402 to the skin.

A tab 446 may be secured to the catheter hub 420, and may extend outwardly from the catheter hub 420. The tab 446 may be integrally formed with the catheter hub 420, or may be formed separately from the catheter hub 420 and attached to the catheter hub 420 through any of various methods known in the art. The tab 446 may extend substantially perpendicular to the catheter hub 420 and/or a cannula axis (not shown) of the cannula 426. Alternatively, the tab 446 may extend at a modest angle away from perpendicular to the catheter hub and/or the cannula axis (e.g. any angle small enough to allow a proximally oriented surface of the tab 446 to serve as a push surface). Thus, the proximally oriented surface of the tab 446 may serve as a push surface, and may be oriented substantially perpendicular to the cannula axis of the cannula 426, or at a modest angle away from perpendicular to the cannula axis, as described. The tab 446 may optionally be positioned proximate the proximal end 430 of the catheter hub 420. Further, if desired, the tab 446 may be positioned nearer to the proximal end 430 of the catheter hub 420 than to the distal end 432 of the catheter hub 420. Positioning of the tab 446 near the proximal end 430 may make the proximally oriented surface of the tab 446 more easily reachable for one or more digits of the hand, such as the thumb.

The needle component 404 may have a needle hub 450, a grip 452, and a needle 454. The needle hub 450 may have a generally cylindrical shape with a proximal end 460 and a distal end 462. The needle hub 450 may also have a boss (not shown) that protrudes from the distal end 462 to interface with the needle port 436 of the catheter hub 420.

The grip 452 may have a generally planar shape, with an irregular, elongated shape when viewed from perpendicular to the plane of the grip 452. The grip 452 may have a proximal portion 466 with a relatively narrow shape, and a distal portion 468 with an enlarged shape. The proximal portion 466 may extend outward from the needle hub 450, and may be generally coplanar with the needle axis (not shown), and thus with the axis of the needle hub 450. The distal portion 468 of the grip 452 may have a leading edge 472, which may serve as a pull surface. The grip 452 may have one or more grip features (not shown), which may help provide a secure interface that facilitates gripping and/or moving the grip 452 by hand.

Further, another tab 474 may be secured to the distal portion 468 of the grip 452. The tab 474 may be integrally formed with the grip 452, or may be formed separately from the grip 452 and attached to the grip 452 through any of various methods known in the art. The tab 474 may extend substantially perpendicular to the plane of the grip 452, or at a modest angle away from perpendicular to the plane of the grip 452 (e.g. any angle small enough to allow a distally oriented surface of the tab 474 to serve as a pull surface). Alternatively, the tab 474 may extend from the grip 452 along a direction nonparallel to the plate of the grip 452. Thus, the distally oriented surface of the tab 474 may serve as a pull surface, and may be oriented substantially perpendicular to the needle axis (not shown) of the needle 454, or at a modest angle away from perpendicular to the needle axis, as described. The location of the tab 474 may facilitate placement of a digit on the distally facing surface of the tab 474, thereby providing enhanced ergonomics, particularly for single-handed operation. The tab 474 and the tab 446 may thus cooperate to facilitate single-handed operation.

The grip 452 and the tab 446 may be rotatable, relative to each other, about the cannula axis of the cannula 426 and the needle axis of the needle 454, which may be coincident in the insertion configuration shown in FIG. 4. Thus, the clinician may rotate the grip 452 and/or the tab 446 to the desired relative orientation prior to insertion and/or prior to motion to the fluid delivery configuration.

If desired, the IV catheter system 400 may have a flash receptacle (not shown), which may be similar to those of previous embodiments. The flash receptacle may receive blood to provide visual confirmation of proper placement of the distal end of the cannula 426.

To move the IV catheter system 400 from the insertion configuration to the fluid delivery configuration, the clinician may position a digit (for example, a finger) on the leading edge 472 of the grip 452 and/or on the tab 474, and a digit (for example, a finger or thumb) on the proximally oriented surface of the tab 446. The proximal/lateral position of the leading edge 472, the tab 474, and/or the tab 446 may facilitate movement to the fluid delivery configuration. The clinician may then pull the leading edge 472 of the grip 452 and/or the tab 474 proximally, and may push and/or brace the proximally oriented surface of the tab 446 distally. This may cause the catheter component 402 to remain in place while the needle component 404 is withdrawn proximally from the catheter component 402.

Figure 5A:
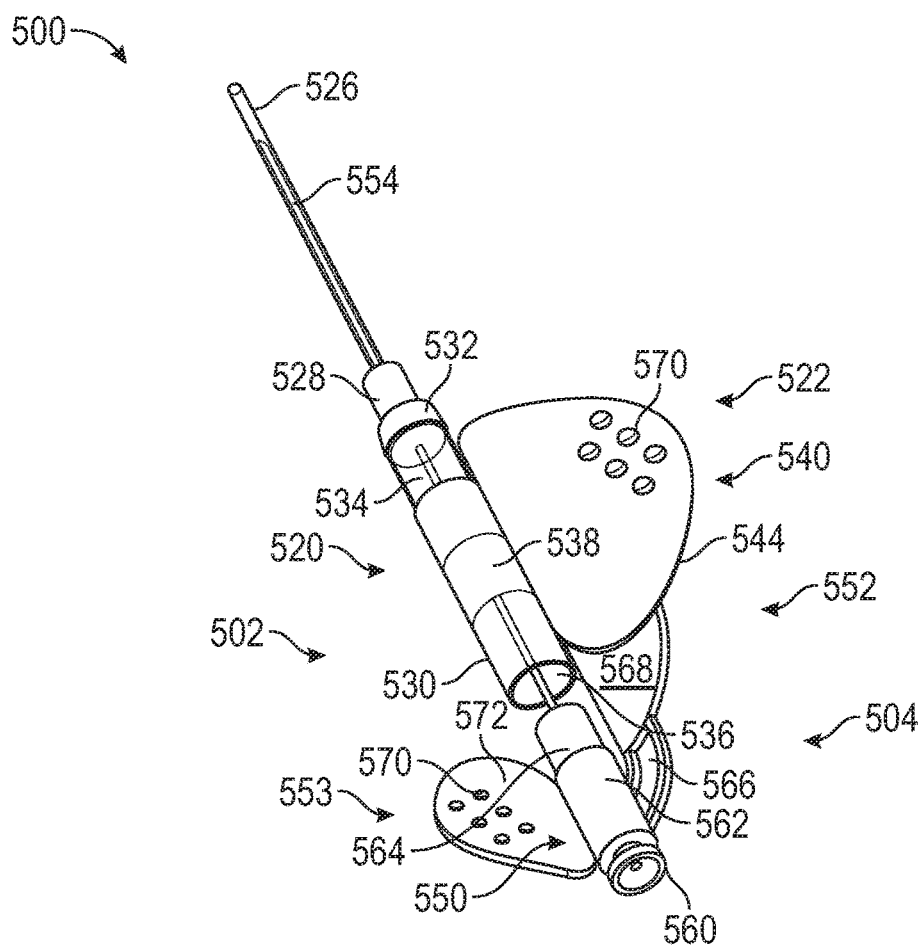
FIGS. 5A and 5B are perspective views of an IV catheter system according to another alternative embodiment.
Figure 5B:
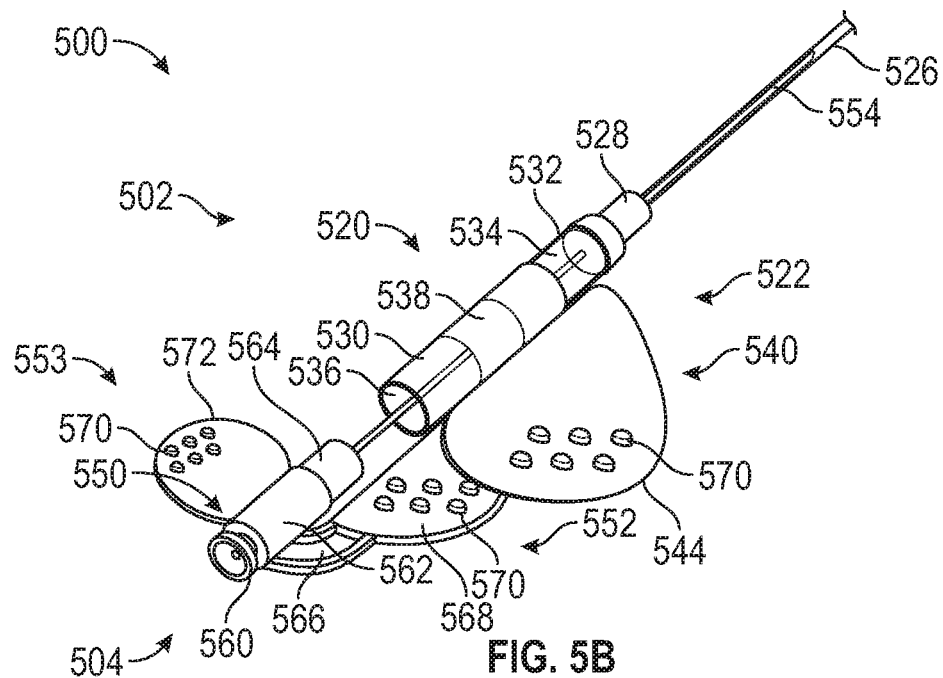

FIGS. 5A and 5B are perspective views of an IV catheter system 500 according to another alternative embodiment. The IV catheter system 500 may have components that generally correspond to those of the IV catheter systems of previous embodiments. FIGS. 5A and 5B show only a catheter component 502 and a needle component 504. Like the IV catheter system 300 of FIG. 3, the IV catheter system 500 may be of an "open" type rather than an "integrated type," and may thus not have pre-attached extension tubing. Rather, extension tubing may be coupled to the proximal end of the catheter component 502 to supply the fluid. The IV catheter system 500 may otherwise have a configuration similar those of previous embodiments; however, some components may be modified, added, or omitted to provide alternative ergonomics and/or functionality.

The catheter component 502 may have a catheter hub 520, a securement platform 522, and a cannula 526. The catheter hub 520 may have a generally tubular and/or hollow conical shape, with a proximal end 530 and a distal end 532. The catheter hub 520 may have a generally translucent exterior wall shaped to define a chamber 534 through which fluid flows to reach the fluid delivery location through the cannula 526. The catheter hub 520 may have a needle port 536 that connects to the needle component 504, proximate the proximal end 530 of the catheter hub 520. The catheter hub 520 may also have a septum 538 positioned within the chamber 534. The septum 538 may be a "low drag" septum as described previously. No extension tubing junction may be present, since the extension tubing is to be coupled to the proximal end 530 of the catheter hub 520.

Further, the catheter hub 520 may have a kink resistance feature that helps to avoid kinking of the cannula 526 during insertion and/or infusion. The kink resistance feature may take the form of a proximal extension 528 on the distal end 532 of the catheter hub 520. The proximal extension 528 may receive the cannula 526, and may provide some resistance to bending of the cannula 526 at the juncture of the cannula 526 to the distal end 532 to relieve the bending strain at that location, thereby helping avoid kinking or other undesired bending of the cannula 526. If desired, the proximal extension 528 may be formed of a more flexible material than that of the remainder of the catheter hub 520, so as to allow some flexure to help prevent kinking.

The securement platform 522 may be attached to the skin of the patient during fluid delivery to keep the cannula 526 in place at the fluid delivery location. The securement platform 522 may have a first wing 540, which may be generally planar in shape. The first wing 540 may have a generally triangular and/or elliptical shape when viewed from perpendicular to the plane of the first wing 540, with a trailing edge 544 that can act as a push surface. The first wing 540 may be coplanar with the cannula axis (not shown) of the cannula 526.

The needle component 504 may have a needle hub 550, a first grip 552, a second grip 553, and a needle 554. The needle hub 550 may have a generally cylindrical shape with a proximal end 560 and a distal end 562. The needle hub 550 may also have a boss 564 that protrudes from the distal end 562 to interface with the needle port 536 of the catheter hub 520.

The first grip 552 may have a generally planar shape, with an irregular, elongated shape when viewed from perpendicular to the plane of the first grip 552. The first grip 552 may have a proximal portion 566 with a relatively narrow shape, and a distal portion 568 with an enlarged shape. The proximal portion 566 may extend outward from the needle hub 550, and may be generally coplanar with the needle axis (not shown), and thus with the axis of the needle hub 550. The distal portion 568 of the first grip 552 may have a leading edge (not shown), which may serve as a pull surface.

The second grip 553 may have a generally planar shape, with generally truncated elliptical shape when viewed from perpendicular to the plane of the second grip 553. The second grip 553 may extend outward from the needle hub 550, and may be generally coplanar with the needle axis (not shown), and thus with the axis of the needle hub 550. The second grip 553 may also be generally coplanar with the first grip 552. The second grip 553 may have a leading edge 572, which may serve as a pull surface. The second grip 553 may be positioned proximally of the first grip 552, though in the insertion configuration, the leading edge 572 of the second grip 553 may still be positioned proximally of the proximal end 530 of the catheter hub 520. Thus, the second grip 553 may provide additional options for a clinician to grasp the needle component 504, particularly during insertion of the IV catheter system 500 and/or motion of the IV catheter system 500 from the insertion configuration to the fluid delivery configuration. In particular, the leading edge 572 of the second grip 553 may be positioned such that a digit of the clinician's hand, such as the thumb, can easily contact and exert proximal pressure on the leading edge 572. Additionally or alternatively, the second grip 553 may facilitate use of a second hand to assist in moving the IV catheter system 500 from the insertion configuration to the fluid delivery configuration.

The first grip 552, the second grip 553, and/or the first wing 540 may have one or more grip features 570, such as raised nubs, bumps, or ridges of any desirable shape and number, or a high-friction surface applied to the first grip 552, the second grip 553, and/or the first wing 540 or from which a portion of the first grip 552, the second grip 553, and/or the first wing 540 may be formed, which may help provide a secure interface that facilitates gripping and/or moving the first grip 552 and/or any other portion of the IV catheter system 500 by hand. The first grip 552 and the second grip 553 may be rigidly secured together via the needle hub 550, but may both be rotatable relative to the first wing 540 about the cannula axis of the cannula 526 and the needle axis of the needle 554, which may be coincident in the insertion configuration shown in FIG. 5A. Thus, the clinician may rotate the first grip 552, the second grip 553, and/or the first wing 540 to the desired relative orientation prior to insertion and/or prior to motion to the fluid delivery configuration.

If desired, the first grip 552 and the first wing 540 may be relatively oriented such that they are parallel or generally parallel to each other, and are positioned in close proximity to each other. Thus, the first grip 552 and the first wing 540 may be positioned in abutting relation to each other in the insertion configuration and during the initial stages of motion from the insertion configuration to the fluid delivery configuration. During motion from the insertion configuration to the fluid delivery configuration, the first grip 552 may slide along the first wing 540. In order to maintain the desired relative positioning between the first grip 552 and the first wing 540, the first grip 552 and/or the first wing 540 may have one or more alignment features (not shown) that maintain relative positioning and/or orientation between the first wing 540 and the first grip 552. Various combinations of ridges, troughs, and/or other features may be used as alignment features.

Such alignment features may help to mitigate the bending moments that may be exerted on the catheter component 502 and/or the needle component 504 by virtue of imbalanced forces applied to the catheter component 502 and/or the needle component 504, thereby helping the catheter component 502 and the needle component 504 remain properly aligned until the IV catheter system 500 is in the fluid delivery configuration. Thus, binding and/or other undesired interactions between the catheter component 502 and the needle component 504 may be avoided during motion from the insertion configuration to the fluid delivery configuration.

Further, the first wing 540 and/or the first grip 552 may have one or more locking features (not shown) that help to keep the IV catheter system 500 in the insertion configuration until the clinician applies a threshold disengagement force sufficient to detach the needle component 504 from the catheter component 502. Various interlocking features such as clips, tabs, detents, recesses, and/or the like may be used as locking features to provide the desired threshold disengagement force.

If desired, the IV catheter system 500 may have a flash receptacle (not shown), which may be similar to those of previous embodiments. The flash receptacle may receive blood to provide visual confirmation of proper placement of the distal end of the cannula 526.

To move the IV catheter system 500 from the insertion configuration to the fluid delivery configuration, the clinician may position a digit (for example, a finger) on the leading edge of the first grip 552 and/or on the leading edge 572 of the second grip 553, and a digit (for example, a finger or thumb) on the trailing edge 544 of the first wing 540. The clinician may then pull the leading edge of the first grip 552 and/or on the leading edge 572 of the second grip 553 proximally, and may push and/or brace the trailing edge 544 of the first wing 540 distally. This may cause the catheter component 502 to remain in place while the needle component 504 is withdrawn proximally from the catheter component 502.

Figure 6:
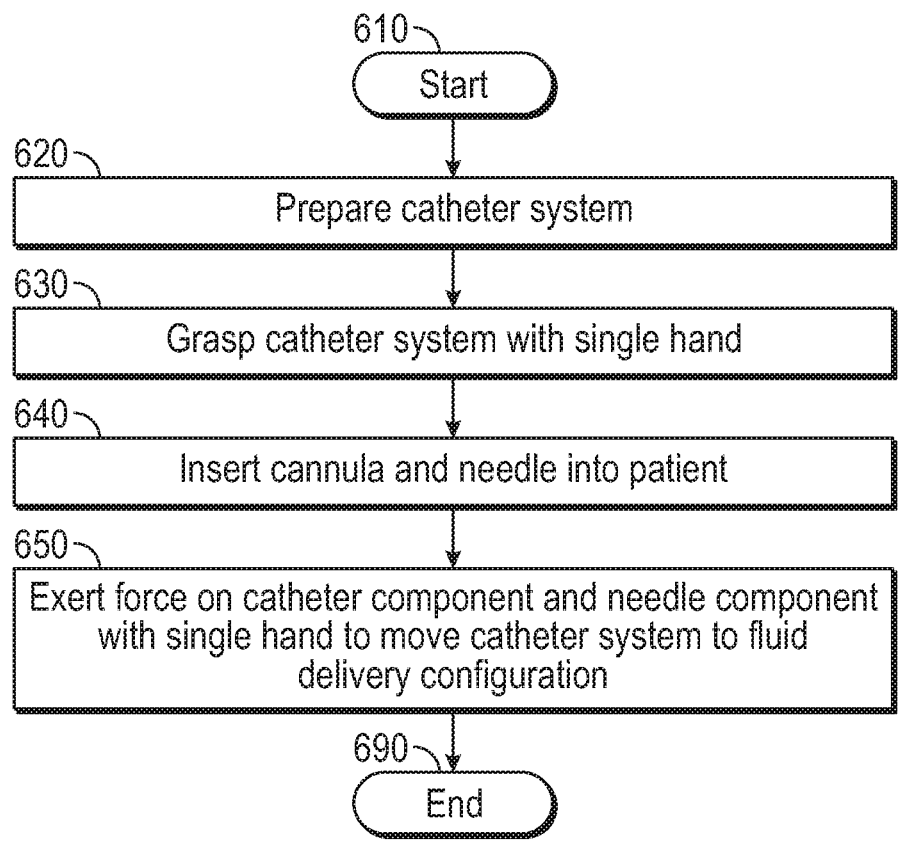
FIG. 6 is a flowchart diagram depicting one method of preparing an IV catheter system to deliver fluid to a patient, according to one embodiment.

FIG. 6 is a flowchart diagram depicting one method of preparing an IV catheter system to deliver fluid to a patient, according to one embodiment. The method of FIG. 6 may be carried out with any of the IV catheter systems disclosed in FIGS. 1 through 5B or with any of the IV catheter systems disclosed with respect FIGS. 7-9B as will be discussed below, or with other IV catheter system embodiments that are not specifically shown or described herein. By way of example, the method will be described in connection with the IV catheter system 100 of FIG. 1. Further, the method of FIG. 6 is merely exemplary; other methods may be used in conjunction with any of the IV catheter system embodiments included within the scope of the present disclosure.

The method may start 610 with a step 620 in which the IV catheter system 100 is prepared. This preparation may include connecting various components (such as the catheter component 102, the needle component 104, the extension tube 106, the clamp 108, the Y adapter 110, and/or the flash receptacle 112 of FIG. 1, by way of example) together. Further, this may include preparing any adhesives needed or desired to secure the catheter component 102 to the patient, preparing components of the fluid source to be connected to the IV catheter system 100, and/or the like.

In a step 630, the IV catheter system 100 may be grasped with a single hand. This may involve placing digits of the hand to contact the pull surface(s) of the needle component 104 and the push surface(s) of the catheter component 102, as described above. Notably, the surfaces that serve as pull surfaces and push surfaces may vary, depending on the specific embodiment utilized. Further, catheter insertion may involve primarily pushing; accordingly, the clinician may elect not to make contact with the pull surfaces at this stage, but to contact them when the IV catheter system 100 is to be moved to the fluid delivery configuration.

In a step 640, the IV catheter system 100 may be manipulated to insert the cannula 126 into the patient. This may optionally be done with a single hand. Insertion may continue until the tip of the cannula 126 has reached the fluid delivery location. Insertion may be carried out by pushing on the push surface(s) and/or other surfaces of the catheter component 102 and/or the needle component 104, and the clinician may further utilize contact with the pull surface(s) of the needle component 104 and/or other surfaces of the catheter component 102 and/or the needle component 104 to steady and/or guide placement of the cannula 126. The clinician may confirm proper insertion of the cannula 126 by observing blood flow into the flash chamber 114 of the flash receptacle 112.

In a step 650, the IV catheter system 100 may be moved from the insertion configuration to the fluid delivery configuration. If the clinician has not yet contacted the pull surface(s) of the needle component 104, he or she may do this now with one or more digits of a hand. Optionally, the same hand used to insert the IV catheter system 100 may be used, exclusively (i.e., without assistance from the other hand) to move the IV catheter system 100 to the fluid delivery configuration. The clinician may pull the pull surface(s) proximally, while pushing or bracing on the push surface(s) to keep the catheter component 102 in place. Thus, the catheter component 102 may be kept in place with the tip of the cannula 126 at the fluid delivery location while the needle component 104 is withdrawn proximally from the catheter component 102 to unblock the fluid delivery path to the fluid delivery location.

This may optionally be accomplished with a single hand. Thus, the other hand may be used to perform other tasks during insertion and/or motion of the IV catheter system 100 to the fluid delivery configuration. For example, the clinician may use the other hand to hold the patient's arm (or other body part in which the fluid delivery location is located), prepare other components for interconnection with the IV catheter system 100, prepare any necessary blood testing materials, and/or the like.

The method may then end 690. With the IV catheter system 100 in the fluid delivery configuration, the fluid source may then be connected to the catheter component 102 to deliver the fluid to the patient, or if the fluid source was previously connected to the catheter component 102, the clamp 108 may be actuated so as to unblock flow from the fluid source to the catheter component 102.

Figure 7A:
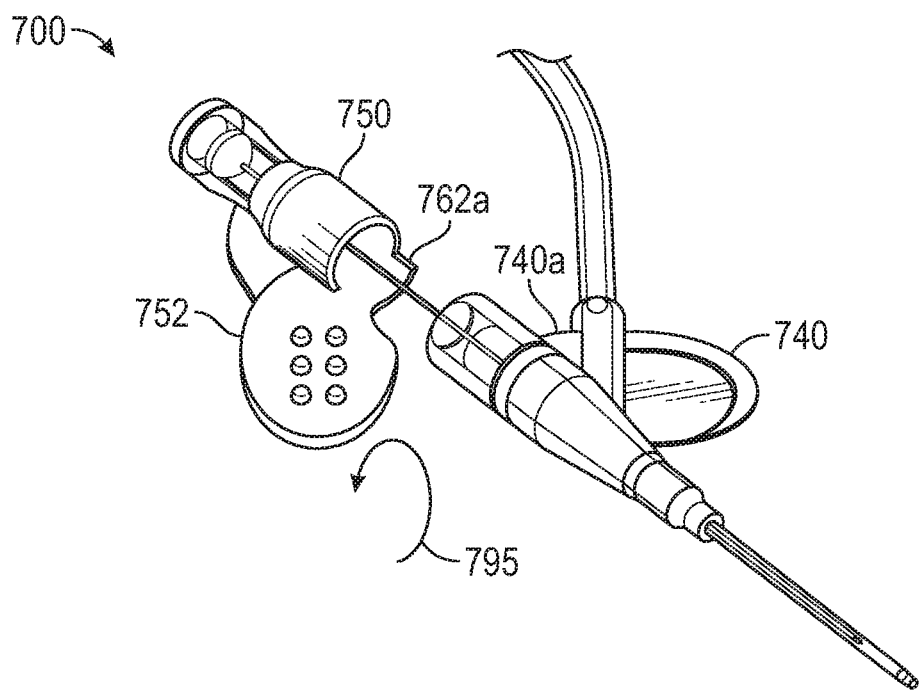
FIG. 7A is a perspective view of an IV catheter system according to another alternative embodiment.

FIG. 7A illustrates another embodiment of an IV catheter system 700 that includes a rotation stop feature 762a formed on needle hub 750. Although the IV catheter system 700 is substantially similar in structure in many regards to the IV catheter system 200, a similar rotation stop feature could also be formed on many of the other above-described embodiments of IV catheter systems. As can be seen in FIG. 7A, many of the features of the IV catheter system 700 are the same as or similar to features of the other IV catheter systems, and therefore these features will not be redundantly described.

The catheter component of the IV catheter system 700 includes a first (or left) wing 740 that is placed similarly to the first wing 240 in the IV catheter system 200. Also, the needle component of the IV catheter system 700 includes a grip 752 that is placed similarly to the grip 252 of the IV catheter system 200. Accordingly, as described above, the needle component can be rotated with respect to the catheter component to position the grip 752 and the first wing 740 in a desired orientation. However, with reference to the design of the IV catheter system 200, one potential drawback of this ability to rotate the needle component 204 is that it allows the grip 252 to freely sag. In other words, while the IV catheter system 200 is being manipulated, the weight of the grip 252 may cause the needle component 204 to rotate to the point that the grip 252 hangs directly below the catheter component 202 thereby making it more inconvenient to position the grip 252 in the appropriate location to manipulate the catheter system 200 to the insertion configuration and/or to the fluid delivery configuration.

To address this issue, IV catheter systems such as the IV catheter system 700 can include the rotation stop feature 762a which functions to limit how far the needle component can rotate in the direction 795 while the needle component is coupled to the catheter component. As shown, the rotation stop feature 762a comprises a distally protruding portion from the distal end of needle hub 750 which forms an upwardly facing ledge that can catch underneath a portion 740a of the first wing 740. In some embodiments, a rotation stop feature of the present invention may comprise a plurality of ledges or other surfaces which are utilized to limit rotation of the needle component.

The rotation stop feature 762a can be positioned so that, when it contacts the portion 740a, the grip 752 will be substantially inline or substantially coplanar with the first wing 740. In other words, the rotation stop feature 762a can retain the grip 752 in a generally flat orientation. However, because the rotation stop feature 762a forms an upwardly facing ledge, it will not prevent the grip 752 from being rotated in a direction opposite the direction 795. Therefore, the grip 752 may still be rotated overtop of the first wing 740 to accommodate different grip techniques.

Alternatively, a rotation stop feature could be formed on the needle component that contacts a different portion of the catheter component. For example, the catheter component can include a protrusion that interfaces with a notch or protrusion formed in the needle component to limit rotation of the needle component in the same manner described above. Also, the rotation stop feature 762a could be configured to contact a portion of the catheter component other than first wing 740.

It is noted that FIG. 7A depicts an embodiment of an IV catheter system that is designed primarily for right-handed insertion. However, the orientation of the components could be reversed in a design that is primarily intended for left-handed insertion. In other words, the first wing 740 and the extension tube could extend from the right side of the catheter component while the grip 752 could extend from the left side of the needle component. In such a design, the rotation stop feature 762a could also be oppositely oriented to prevent over-rotation in the direction opposite the direction 795. Also, a similar rotation stop feature could be incorporated into the other embodiments of IV catheter systems described herein.

Figure 7B:
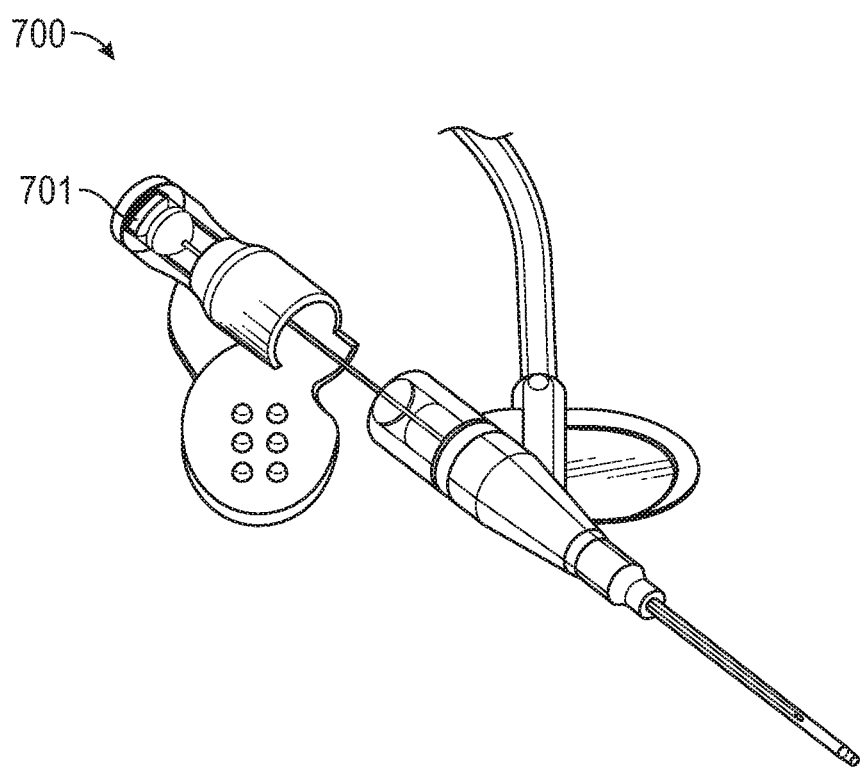
FIG. 7B is a perspective view of an IV catheter system according to another alternative embodiment.

FIG. 7B illustrates an embodiment of an IV catheter system 700 that includes a flash receptacle having a side vent 701. Although the IV catheter system 700 is configured in many regards similar to the IV catheter system 700 of FIG. 7A, a similar side vent could be incorporated into any of the above-described embodiments having a needle component that includes a flash chamber.

Although not visible in FIG. 7B, the proximal end of the needle component can include an opening through which air can be vented as flash flows into the flash chamber formed within the flash receptacle of the needle component. In some gripping techniques, the clinician may place a digit (e.g., the thumb or a finger) overtop this proximal opening thereby minimizing or preventing the venting of air from the flash chamber. To address this, the flash receptacle of the IV catheter system 700 of FIG. 7B can include one or more side vents 701 which may function to vent air from the flash chamber even if the proximal opening is covered. Each of the side vents 701 can be positioned proximal to any membrane or other blood-flow-inhibiting structure contained within the flash chamber so that blood is prevented from exiting through the side vent 701. In some embodiments, the flash receptacle may not include a proximal opening and therefore may rely only on the one or more side vents 801 for venting.

Figure 8:
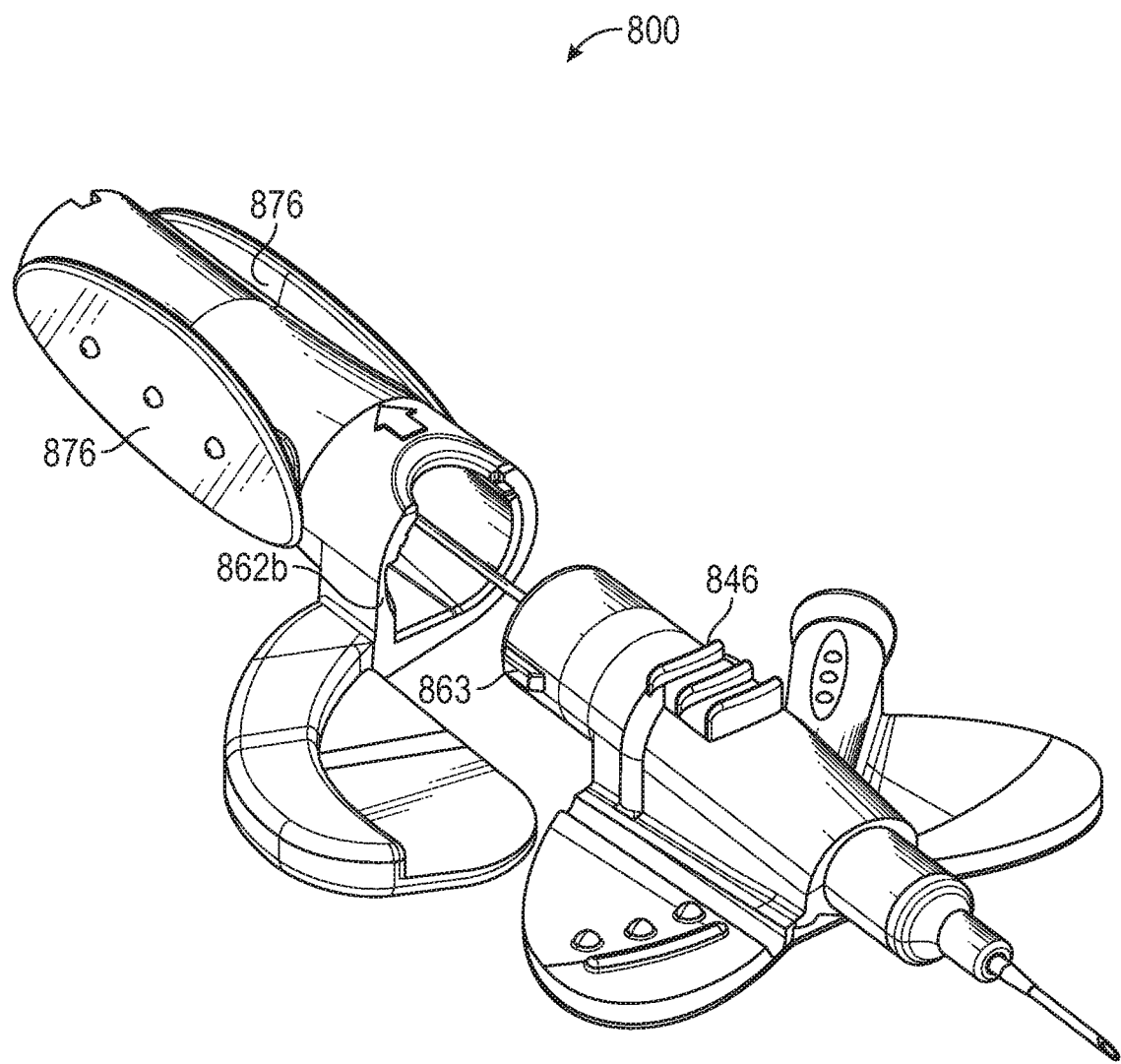
FIG. 8 is a perspective view of an IV catheter system according to another alternative embodiment.

FIG. 8 illustrates an embodiment of an IV catheter system 800 that includes an alternative rotation stop feature 862*b* formed as an internal notch on the needle hub. The IV catheter system 800 also includes a corresponding rotation stop feature on the catheter hub, in this case tab 863. As illustrated in FIG. 8, the rotation stop feature 862*b* and the notch 863 may be formed to essentially entirely prevent any rotation of the needle hub relative to the catheter hub. In other words, the notch of rotation stop feature 862*b* may be limited in size to prevent more than minimal rotation. In other embodiments, the notch of rotation stop feature 862*b* may be enlarged circumferentially to permit any desired extent of rotation of the needle hub relative to the catheter hub. The IV catheter system 800 may have components that generally correspond to those of the IV catheter systems of previous embodiments, and such features will not be redundantly described. While the IV catheter system 800 of FIG. 8 may be of the integrated type, the additional features discussed with respect to the catheter system 800 may also be applied to alternative embodiments including open and safety integrated IV catheter systems.

In some embodiments one or more additional features may be provided to serve as push and/or pull surfaces to facilitate one-handed motion of the IV catheter system between the insertion configuration and the fluid delivery configuration. For example, the flash receptacle of the various embodiments described above may be replaced with a cylindrical low-volume/high-visualization flash chamber that is adapted to be inserted into the needle component. Additionally, one or more grips may be applied to sides of the flash receptacle and/or other portions of the needle component to facilitate a central grip insertion technique where the side grips of the flash receptacle/needle component are used in insertion and/or moving to the fluid delivery configuration. Additionally, a further example of a push surface may be provided in the form of a raised circumferential ring of soft and/or flexible material applied to the catheter hub of the catheter component. In some embodiments, the soft and/or flexible material comprises a durometer hardness of from approximately 30 Shore A to approximately 90 Shore D. In some embodiments, the soft and/or flexible material comprises a durometer hardness of from approximately 50 Shore A to approximately 90 Shore D. Any further modification provided to any component to provide further surfaces on which to push or pull to accomplish techniques similar to those discussed herein are embraced as falling within the spirit of the invention.

Figure 9A:
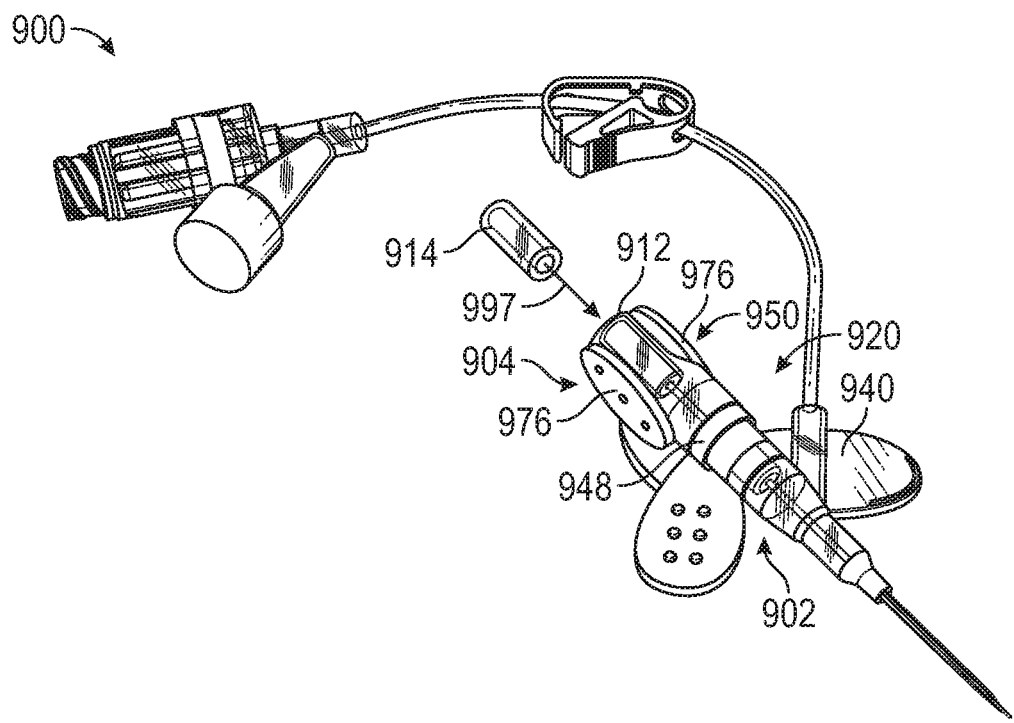
FIGS. 9A and 9B are perspective views of an IV catheter system according to another alternative embodiment.
Figure 9B:
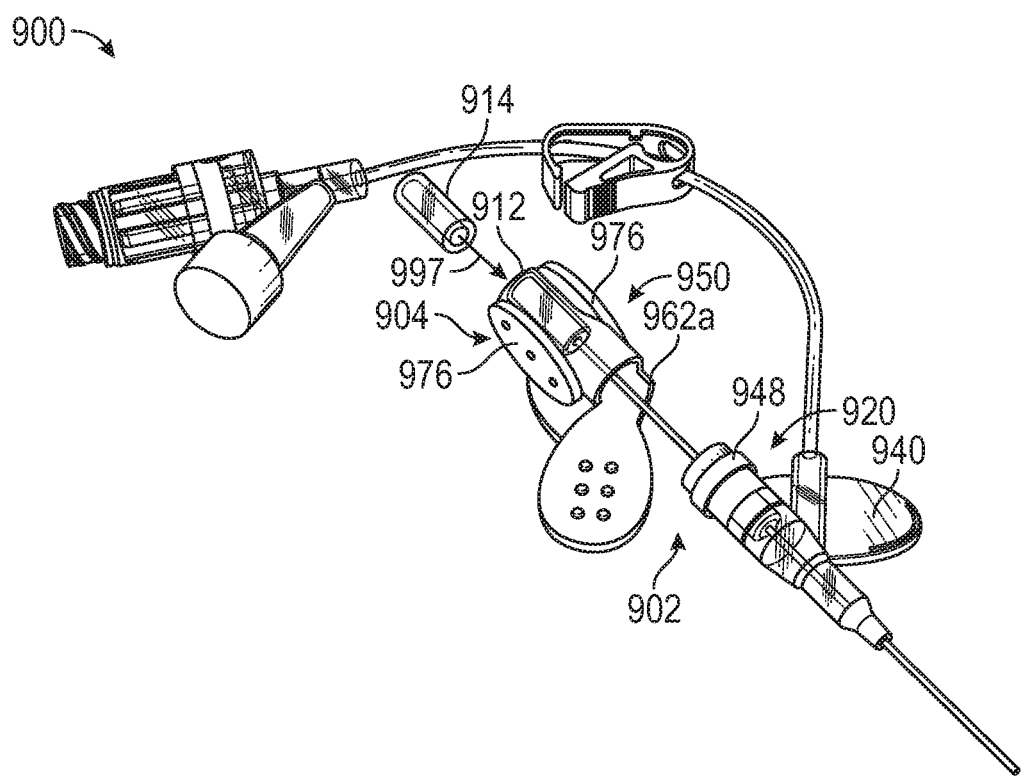

FIGS. 9A and 9B are perspective views of an IV catheter system 900 according to another alternative embodiment. The IV catheter system 900 may have components that generally correspond to those of the IV catheter systems of previous embodiments, and such features will not be redundantly described. While the IV catheter system 900 of FIGS. 9A and 9B may be of the integrated type, the additional features discussed with respect to the catheter system 900 may also be applied to alternative embodiments including open and safety integrated IV catheter systems.

As discussed with the IV catheter systems 700 of FIGS. 7A and 7B, a catheter component 902 of the IV catheter system 900 includes a wing 940 that is adapted to contact a corresponding rotation stop feature 962*a* of a needle component 904. The rotation stop feature 962*a* functions with the wing 940 to limit how far the needle component can rotate relative to the catheter component while the needle component is coupled to the catheter component. The function of the rotation stop feature 962*a* is essentially similar to the function of the rotation stop feature 762*a*.

The catheter component 902 includes an additional feature that may serve as a push feature that facilitates movement of the IV catheter system 900 from the insertion configuration generally shown in FIG. 9A to the fluid delivery configuration, the movement between configurations being illustrated in FIG. 9B. The additional feature is a circumferential ring 948 disposed around a catheter hub 920 of the catheter component 902. The circumferential ring 948 may be manufactured of a material that is relatively soft to the touch and/or that provides a relatively high coefficient of friction to facilitate secure reception of a tip of a digit thereon to facilitate movement of the IV catheter system 900 from the insertion configuration to the fluid delivery configuration. Additionally or alternatively, the circumferential ring 948 may be formed of a relatively rigid material. Additionally or alternatively, the circumferential ring 948 may be formed with a textured surface, such as a surface having ridges, bumps, or nubs.

Additional features are also provided to the needle component 904 that may serve as additional pull features to facilitate movement of the IV catheter system 900 from the insertion configuration to the fluid delivery configuration. Specifically, a pair of central grips 976 may be affixed to opposing sides of a needle hub 950 of the needle component 904. The central grips 976 may be formed of a material that is relatively soft to the touch and/or that provides a relatively high coefficient of friction to facilitate securing the needle component 904 by gripping the central grips 976 in a pinching motion, whereby a pulling force can be applied to the needle component 904 while a pushing or bracing force is applied to the catheter component 902, such as using the circumferential ring 948. Additionally or alternatively, the central grips 976 may be formed of a relatively rigid material. Additionally or alternatively, the central grips 976 may be formed with a textured surface, such as a surface having ridges, bumps, or nubs, as is illustrated in FIGS. 9A and 9B.

The additional push and pull features illustrated in FIGS. 9A and 9B provide alternative mechanisms by which the IV catheter system 900 may be inserted in the insertion configuration and/or moved from the insertion configuration to the fluid delivery configuration with a single hand. In some alternative embodiments of an IV catheter system, some of the various push and pull features discussed herein may be omitted in favor of the additional push and pull features discussed with respect to FIGS. 9A and 9B. Thus, the specific combination of push and pull features illustrated in FIGS. 9A and 9B is not intended to be limiting of the use of circumferential rings such as circumferential ring 948 and/or central grips such as central grips 976, as may be illustrated by the inclusion of central grips 876 on the IV catheter system 800 of FIG. 8 without the inclusion of a corresponding circumferential ring, but instead with the inclusion of tabs 846 analogous to the tab 446 of the IV catheter system 400 of FIG. 4.

FIGS. 9A and 9B illustrate an additional feature that may be incorporated into certain embodiments of IV catheter systems, namely a low-volume high-visualization flash chamber 914. The low-volume high-visualization flash chamber 914 may be fixedly or removably received within a flash receptacle 112 of the needle hub 950 of the needle component 904. When the low-volume high-visualization flash chamber 914 is removably received in the flash receptacle 112, it may be inserted through an opening in a proximal end of the needle hub 950, as illustrated by direction 997.

Various embodiments of the present invention may further comprise a needle safety mechanism configured to secure the sharpened, distal tip of the introducer needle following removal and separation of the various embodiments of the needle component from the various embodiments of the catheter component to prevent accidental needle sticks. A safety mechanism may include any compatible device known in the art. In some instances, the safety mechanism is configured to interact with a needle feature, such as a ferrule, notch, crimp or bump on the needle. The crimp or bump formed in the needle causes a slight out of round configuration that can be used to activate a safety mechanism. In some instance, the safety mechanism comprises an arm or lever that is actuated to capture the needle tip within the mechanism and prevent the tip from emerging prior to safe disposal.

The safety mechanism may be coupled with the particular IV catheter system in any number of ways. In some embodiments, the safety mechanism may include an internal interlock in which the safety mechanism is coupled with an internal surface of a catheter component. Coupling may include threading, fitting, snapping, connecting, attaching, fastening, clipping, hooking, or any other suitable means of coupling. Non-limiting examples of safety mechanisms that include an internal interlock are provided in: U.S. Pat. No. 8,496,623, titled BI-DIRECTIONAL CANNULA FEATURE CAPTURE MECHANISM, filed Mar. 2, 2009; U.S. Pat. No. 9,399,120, titled BI-DIRECTIONAL CANNULA FEATURE CAPTURE MECHANISM, filed Jul. 11, 2013; U.S. Patent Application No. 62/314,262, titled CANNULA CAPTURE MECHANISM, filed Mar. 28, 2016, each of which is herein incorporated by reference in its entirety. In some embodiments, the safety mechanism may include a clip disposed within the catheter component, a non-limiting example of which is provided in U.S. Pat. No. 6,117,108, titled SPRING CLIP SAFETY IV CATHETER, filed Jun. 12, 1998, which is herein incorporated by reference in its entirety.

In some embodiments, the safety mechanism may include an external interlock in which the safety mechanism is coupled with an external surface of the catheter component. In some embodiments, the safety mechanism may be coupled with an external surface of the catheter component and an internal and/or external surface of a needle hub. Coupling may include threading, fitting, snapping, connecting, attaching, fastening, clipping, hooking, or any other suitable means of coupling. Non-limiting examples of safety mechanisms that include an external interlock are provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the safety mechanism may include a V-clip or a similar clip. A non-limiting example of a V-clip is provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. The V-clip may selectively retain a portion of the catheter component.

In some embodiments, a defeatable mechanical connection is provided between the safety mechanism and at least one other component of the IV catheter system. In some instances, the mechanical connection is defeated upon securement of the distal tip of the needle within the safety mechanism. In some embodiments, a surface of the safety mechanism is selectively coupled to one or more of the following: the catheter component, a blood control valve, an extension tube, and one or more paddle grips.

In some embodiments, the safety mechanism may include a safety barrel, which may be spring-loaded. For example, the safety barrel may be spring loaded as in the BD™ Insyte® Autoguard™ BC shielded protective IV catheter. In some embodiments, the safety mechanism may be passively and/or actively activated. In some embodiments, the safety mechanism may be configured to interact with a needle feature, such as a ferrule, notch, crimp or bump on the needle. In some embodiments, the safety mechanism may include an arm or lever that may be actuated to capture the distal tip within the safety mechanism and prevent the tip from emerging prior to safe disposal. In some embodiments, the safety mechanism may be attached to a body of the needle and may be capable of sliding along the length thereof.

In some embodiments, in an assembled position prior to catheterization, the safety mechanism may be disposed between the catheter component and the needle hub. In some embodiments, the catheter component and the needle hub may be spaced apart by at least a portion of the safety mechanism in the assembled position prior to catheterization. In some embodiments, in the assembled position prior to catheterization, a proximal end of the catheter component may be disposed between a distal end of the safety mechanism and a distal end of a grip of the needle hub, such as, for example, a paddle grip. In some embodiments, in the assembled position prior to catheterization, the proximal end of the catheter component may be disposed between the distal end of the safety mechanism and a proximal end of the grip of the needle hub. In some embodiments, a portion of the safety mechanism may overlap with a portion of the grip of the needle hub. In some embodiments, at least a portion of at least one of the catheter component and the grip overlaps at least some portion of the safety mechanism. In some embodiments, no portion of the catheter component or the grip overlaps any portion of the safety mechanism.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:

1. An intravenous (IV) catheter system comprising an insertion configuration and a fluid delivery configuration, the IV catheter system comprising:
 a catheter component comprising:
  a catheter hub comprising a catheter hub distal end and a catheter hub proximal end, wherein the catheter hub defines a chamber extending between the catheter hub distal end and the catheter hub proximal end, and a needle port at the catheter hub proximal end that provides access to the chamber;

a cannula extending distally from the catheter hub distal end; and a wing extending outwardly from the catheter hub, wherein an upper surface of the wing comprises a push feature defining a push surface of the catheter component, wherein the push feature comprises a tab oriented generally perpendicular to a longitudinal axis of the cannula, extending upwardly from the wing, and spaced apart from the longitudinal axis of the cannula;

a needle component comprising:

a needle hub comprising a needle hub distal end;

a needle extending distally from the needle hub distal end; and a grip having a generally planar shape and extending outwardly from the needle hub, wherein an upper surface of the grip comprises a pull feature connected to the needle hub and defining a pull surface of the needle component;

wherein, in the insertion configuration, the needle is positioned within the cannula, the needle hub distal end is seated in the needle port, and the pull surface is positioned distal the catheter hub proximal end.

2. The IV catheter system of claim 1, wherein the pull surface is positioned distal the push surface when the IV catheter system is in the insertion configuration.

3. The IV catheter system of claim 1, wherein the push feature is integrated into a securement platform comprising a wing extending from the catheter hub generally parallel to a cannula axis along which the cannula extends such that, in the fluid delivery configuration, the wing rests on skin of a patient receiving fluid through the IV catheter system.

4. The IV catheter system of claim 3, wherein the wing is integrated with an extension tubing junction extending outwardly from the catheter hub at a location intermediate the catheter hub distal end and the catheter hub proximal end.

5. The IV catheter system of claim 3, wherein the wing is not coplanar with a cannula axis containing the cannula.

6. The IV catheter system of claim 1, wherein the catheter component further comprises a septum within the chamber through which the needle passes in the insertion configuration and wherein the septum is configured to provide a sufficiently low resistance to withdrawal of the needle through the septum to enable a single hand of a clinician to move the IV catheter system from the insertion configuration to the fluid delivery configuration without assistance of another hand of the clinician.

7. The IV catheter system of claim 1, wherein the pull feature comprises a feature selected from the group consisting of:

a leading edge of a grip secured to the needle hub and extending outwardly and generally distally from the needle hub;

a grip feature applied to or formed on a major surface of a grip secured to the needle hub and extending outwardly and generally distally from the needle hub;

a series of nubs applied to or formed on a major surface of a grip secured to the needle hub and extending outwardly and generally distally from the needle hub;

a tab secured to a grip, the grip being secured to the needle hub and extending outwardly and generally distally from the needle hub generally parallel to an axis of the needle, and the tab extending from the grip in a direction nonparallel to the grip; and a tab secured to a grip, the grip being secured to the needle hub and extending outwardly and generally distally from the needle hub generally parallel to an axis of the needle, and the tab extending substantially perpendicularly from the grip.

8. The IV catheter system of claim 1, wherein:

the catheter component comprises a wing extending outwardly from the catheter hub generally parallel to a cannula axis;

the needle component comprises a grip extending outwardly and distally from the needle hub generally parallel to a needle axis;

in the insertion configuration, the wing and the grip are generally parallel to each other and are positioned in abutting relation to each other; and during motion of the IV catheter system from the insertion configuration to the fluid delivery configuration, the grip slides along the wing.

9. The IV catheter system of claim 1, wherein the needle component comprises a rotation stop feature formed proximate the needle hub distal end, the rotation stop feature being configured to engage a corresponding feature on the catheter component to limit rotation of the needle component relative to the catheter component.

10. The IV catheter system of claim 9, wherein:

the catheter component comprises a wing extending outwardly from the catheter hub generally parallel to a cannula axis;

the needle component comprises a grip extending outwardly and distally from the needle hub generally parallel to a needle axis;

the rotation stop feature extends distally from the needle hub distal end;

in the insertion configuration, the needle component is rotated relative to the catheter component such that the rotation stop feature contacts the wing of the catheter component and the grip is substantially co-planar with the wing.

11. The IV catheter system of claim 10, further comprising:

a circumferential ring extending around the catheter hub;

a low-drag septum disposed within the catheter hub;

opposed side grips disposed on opposing sides of the needle hub; and a low-volume, high-visualization flash chamber removably attached to a flash receptacle attached to a proximal end of the needle hub.

12. The IV catheter system of claim 1, wherein the needle component comprises a needle hub proximal end having a flash receptacle containing a flash chamber.

13. The IV catheter system of claim 12, wherein the flash receptacle includes one or more side vents for venting air from the flash chamber.

14. An intravenous (IV) catheter system comprising an insertion configuration and a fluid delivery configuration, the IV catheter system comprising:

a catheter component comprising:

a catheter hub comprising a catheter hub distal end and a catheter hub proximal end, wherein the catheter hub defines a chamber extending between the catheter hub distal end and the catheter hub proximal end, and a needle port at the catheter hub proximal end that provides access to the chamber;

a cannula extending distally from the catheter hub distal end; and a wing connected to the catheter hub and extending outwardly from the catheter hub, wherein an upper surface of the wing comprises a push surface of the catheter component;

a needle component comprising:
  a needle hub comprising a needle hub distal end;
  a needle extending distally from the needle hub distal end; and
  a grip connected to the needle hub, wherein the grip is generally planar, wherein the grip comprises a proximal portion extending outwardly and distally from the needle hub, wherein the grip further comprises a distal portion having an enlarged shape compared to the proximal portion, wherein an upper surface of the grip comprises a pull surface of the needle component;

wherein, in the insertion configuration, the needle is positioned within the cannula, the needle hub distal end is seated in the needle port, and the pull surface is positioned distal the catheter hub proximal end.

15. The IV catheter system of claim 14, wherein the pull surface is positioned distal the push surface when the IV catheter system is in the insertion configuration.

16. The IV catheter system of claim 14, wherein the pull surface comprises a surface selected from the group consisting of:
  a leading edge of the grip;
  a grip feature applied to or formed on a major surface of the grip;
  a series of nubs applied to or formed on a major surface of the grip;
  a tab secured to the grip, the tab extending from the grip in a direction nonparallel to the grip; and
  a tab secured to the grip, the tab extending substantially perpendicularly from the grip.

17. An intravenous (IV) catheter system comprising:
a catheter component comprising:
  a catheter hub having a proximal end;
  a cannula that extends distally from the catheter hub; and
  a wing that extends outwardly from a side of the catheter hub; and
a needle component comprising:
  a needle hub having a distal end that couples to the proximal end of the catheter hub;
  a needle that extends distally from the distal end of the needle hub;
  a grip that extends outwardly and distally from a side of the needle hub; and
  a rotation stop feature formed at the distal end of the needle hub, the rotation stop feature being adapted to contact the wing of the catheter component to limit rotation of the needle component with respect to the catheter component when the needle is fully inserted in the cannula, wherein the rotation stop feature is positioned such that the grip is substantially coplanar with the first wing when the rotation stop feature contacts the wing, wherein the rotation stop feature comprises a protrusion; and
  a notch, wherein the rotation stop feature is movable within the notch to allow rotation to the needle hub with respect to the catheter hub, wherein movement of the rotation stop feature is limited to the notch.

18. The IV catheter system of claim 17, wherein:
the rotation stop feature extends distally from the distal end of the needle hub; and
when the rotation stop feature contacts the wing, a plane of the grip is substantially parallel to a plane of the wing.

* * * * *